(12) United States Patent
Sehgal

(10) Patent No.: US 8,715,920 B2
(45) Date of Patent: *May 6, 2014

(54) COMPOSITION FOR PRESERVING PLATELETS DURING PHOTOSENSITIZATION

(75) Inventor: Lakshman R. Sehgal, Monarch Beach, CA (US)

(73) Assignee: Biovec Transfusion, LLC, Chicago, IL (US)

( * ) Notice: Subject to any disclaimer, the term of this patent is extended or adjusted under 35 U.S.C. 154(b) by 272 days.

This patent is subject to a terminal disclaimer.

(21) Appl. No.: 13/180,389

(22) Filed: Jul. 11, 2011

(65) Prior Publication Data

US 2012/0028236 A1 Feb. 2, 2012

Related U.S. Application Data

(60) Provisional application No. 61/368,078, filed on Jul. 27, 2010.

(51) Int. Cl.
*A01N 1/02* (2006.01)

(52) U.S. Cl.
USPC .......................................................... 435/2

(58) Field of Classification Search
None
See application file for complete search history.

(56) References Cited

U.S. PATENT DOCUMENTS

| | | | |
|---|---|---|---|
| 5,179,120 A | 1/1993 | Vogel et al. | |
| 5,242,810 A | 9/1993 | Maraganore et al. | |
| 5,378,601 A | 1/1995 | Gepner-Puszkin | |
| 5,798,238 A | 8/1998 | Goodrich, Jr. et al. | |
| 5,869,701 A | 2/1999 | Park et al. | |
| 5,955,256 A | 9/1999 | Sowemimo-Coker et al. | |
| 5,981,163 A | 11/1999 | Horowitz et al. | |
| 6,001,882 A | 12/1999 | Fox et al. | |
| 6,030,767 A | 2/2000 | Wagner et al. | |
| 6,087,141 A | 7/2000 | Margolis-Nunno et al. | |
| 6,106,773 A | 8/2000 | Miekka et al. | |
| 6,548,241 B1 | 4/2003 | McBurney et al. | |
| 7,964,338 B2 * | 6/2011 | Sehgal et al. | 435/2 |
| 8,129,104 B2 * | 3/2012 | Sehgal et al. | 435/2 |
| 8,142,992 B2 * | 3/2012 | Sehgal et al. | 435/2 |
| 8,329,389 B2 * | 12/2012 | Sehgal | 435/2 |
| 2003/0215785 A1 | 11/2003 | Goodrich et al. | |
| 2006/0177811 A1 * | 8/2006 | Sehgal et al. | 435/2 |
| 2009/0253115 A1 | 10/2009 | Sehgal et al. | |

FOREIGN PATENT DOCUMENTS

| | | | |
|---|---|---|---|
| WO | WO 96/13158 | * | 5/1996 |
| WO | 00/04930 A2 | | 2/2000 |
| WO | 03/090794 A1 | | 11/2003 |
| WO | 2006/076401 A2 | | 7/2006 |
| WO | WO 2006/076401 | * | 7/2006 |

OTHER PUBLICATIONS

Picker et al., "Cell viability during platelet storage in correlation to cllular metabolism after different pathogen reduction technologies", Transfusion 49 : 2311-2318 (2009).*
Li et al., "Platelet glycolytic flux increases stimulated by ultraviolet-induced stress is not the direct cause of platelet morphology and activation changes: possible implications for the role of glucose in platelet storage", Transfusion 45 : 1750-1758 (2005).*
Men'shikov et al., "The calcium blocking effect of nitrocompounds on human platelets: correlation with changes in the cyclic guanosine monophosphate content", Biokhimiya (Moscow) 52 (3) : 430-436 (1987), CA abstract only.*
Bode et al., "Preservation of in vitro function of platelets stored in the presence of inhibitors of platelet activation and a specific inhibitor of thrombin", J. Lab. Clin. Med. 111 (1) 118-124 (1988).*
Cattaneo et al., "Ticlopidine selectively inhibits human platelet responses to adenosine diphosphate", Thrombosis and Haemostasis 66 (6) : 694-699 (1991), Biosis abstract only.*
International Search Report and Written Opinion of the International Search Authority, mailed Feb. 28, 2012 (International Application No. PCT/US2011/043669, filed Jul. 12, 2011).
Nagahara, T. et al., "Anticoagulant Factor Xa Inhibitor," Drugs of the Future, 20(6): 564-566, (1995).
Pruitt, J.R. et al., "Isoxazolines and Isoxazoles as Factor Xa Inhibitors," Bioorganic & Medicinal Chemistry Letters, 10: 685-689, (2000).
Quan, M.L. et al., "Design and Synthesis of Isoxazoline Derivatives as Factor Xa Inhibitors. 1" J Med. Chem. 42: 2752-2759, (1999).
Sato, K. et al., "Relationship between the antithrombotic effect of YM-75466, a novel factor Xa inhibitor, and coagulation parameters in rats," European Journal of Pharmacology, 347: 231-236, (1998).
Wong, P.C. et al., "Nonpeptide Factor Xa Inhibitors: 1. Studies with SF303 and SK549, a New Class of Potent Antithrombotics," Journal of Pharmacology and Experimental Therapeutics, 292(1):351-357, (2000).
Herbert, J. M. et al., "DX 9065A, a Novel, Synthetic, Selective and Orally Active Inhibitor of Factor Xa: In Vitro and in Vivo Studies," Journal of Pharmacology and Experimental Therapeutics, 276(3):1030-1038 (1996).
Nagahara, T. et al., "Design, Synthesis and Biological Activities of Orally Active Coagulation Factor Xa Inhibitors," Eur. J. Med. Chem. 30(suppl):140s-143s (1995).
Ewing, W.R. et al., "Progress in the design of inhibitors of coagulation factor Xa," Drugs of Future 24(7):771-787 (1999).
Ostrem, J.A. et al., "Characterization of an orally available and highly specific synthetic factor Xa Inhibitor," Thromb. Haemost. 73:1306 (1995).
Krishnamurti, C. et al., "Reduction of blood loss by infusion of human platelets in a rabbit kidney injury model," Transfusion, 39:967-974 (1999).

(Continued)

*Primary Examiner* — Sandra Saucier
(74) *Attorney, Agent, or Firm* — Ping Wang; Andrews Kurth, LLP

(57) ABSTRACT

A platelet preservation composition is disclosed. The composition comprises a photosensitizer, an inhibitor of platelet activation, and/or an anticoagulant. The preservation composition allows inactivation of pathogens in a platelet preparation while maintaining the functionality of the platelets.

5 Claims, 8 Drawing Sheets
(7 of 8 Drawing Sheet(s) Filed in Color)

(56) References Cited

OTHER PUBLICATIONS

Al-Obeidi, F et al., "Factor Xa Inhibitors," Expert Opinion on Therapeutic Patents 9(7):931-953 (1999).

Pinto, D.J.D., et al., "Discovery of 1-[3-(Aminomethyl)phenyl]-N-[3-fluoro-2'-(methylsulfonyl)- [1,1'-biphenyl]-4-yl]-3-(trifluoromethyl)-1H-pyrazole-5-carboxamide (DPC423), a Highly Potent, Selective, and Orally Bioavailable Inhibitor of Blood Coagulation Factor Xa," J. Med. Chem., 2001, 44 (4), pp. 566-578.

Warnhotlz, et al. "Vasoactive Role of the $\alpha v \beta 3$ iNtegrin in Rabbit Carotid Artery: Endothelium-Dependent and Independent Effects," Supplement to Circulation: Abstract 179, vol. 98, No. 17, Oct. 27, 1998.

Hirsh, et al. "New antithrombotic agents," The Lancet, vol. 353, pp. 1431-1436 (1999).

Fareed, et al. "New antithrombotic drugs: A perspective," Current Opinion in Cardiovascular, pulmonary, and renal investigational drugs, 1 (1): 40-55 (1999).

Extended European Search Report issued on Nov. 25, 2013, in European Patent Application No. 11814977.2 (filed Jul. 12, 2011).

\* cited by examiner

COMPOSITION FOR PRESERVING PLATELETS DURING PHOTOSENSITIZATION

This application claims priority from U.S. Provisional Application Ser. No. 61/368,078, filed on Jul. 27, 2010. The entirety of that provisional application is incorporated herein by reference.

FIELD

The present invention relates to a composition and method for maintaining platelet functionality and extending the shelf-life of platelets. More particularly, the present invention relates to a preservation composition comprising a photosensitizer, an inhibitor of platelet activation, and an anticoagulant.

BACKGROUND

When blood vessels are damaged, cell fragments released from the bone marrow, called platelets, adhere to the walls of blood vessels and form clots to prevent blood loss. It is important to have adequate numbers of normally functioning platelets to maintain effective clotting, or coagulation, of the blood. Occasionally, when the body undergoes trauma, or when the platelets are unable to function properly, it is necessary to replace or transfer platelet components of blood into a patient. Most commonly, platelets are obtained from volunteer donors either as a component of a whole blood unit, or via plateletpheresis (withdrawing only platelets from a donor and re-infusing the remaining of the blood back into the donor). The platelets then are transferred to a patient as needed, a process referred to as "platelet transfusion."

Platelet transfusion is indicated under several different scenarios. For example, an acute blood loss, either during an operation or as a result of trauma, can cause the loss of a large amount of platelets in a short period of time. Platelet transfusion is necessary to restore a normal ability to control blood flow, or haemostasis. In a medical setting, an individual can develop a condition of decreased number of platelets, a condition known as thrombocytopenia. The condition can occur as a result of chemotherapy, and requires platelet transfusion to restore normal blood clotting.

Unlike red blood cells, which can be stored for forty-five (45) days, platelets can be stored for a few days. Platelet sterility is difficult to maintain because platelets cannot be stored at low temperatures, for example 4° C. to 5° C. A low storage temperature for the platelets initiates an activation process within the platelets that leads to aggregation and cell death. Bacterial growth in the platelet medium at suitable storage temperatures, e.g., room temperature, can lead to an unacceptable occurrence of bacterial contamination in platelets used for transfusion. In fact, bacterial contamination of platelet products has been recognized as the most frequent infectious risk from transfusion, occurring in approximately 1 of 2000 to 1 of 3000 whole blood derived random donor platelets or apheresis derived single donor platelets. In the U.S.A., bacterial contamination is considered to be the second most common cause of death overall, from transfusion, with mortality rates ranging from 1:20,000 to 1:85,000. As a result, the Food and Drug Administration (FDA) limits the storage time of platelets to five (5) days, thereby safeguarding the transfusion supply from bacterial contamination.

Many sterilization methods have been suggested. Platelet compositions typically can be sterilized by radiation, chemical sterilization, or a combination thereof. For example, a method of inactivating viral and bacterial blood contaminants using a quinoline as a photosensitizer is disclosed in U.S. Pat. No. 5,798,238. Other classes of photosensitizers are, for example, psoralens, coumarins, or other polycyclic ring compounds, as disclosed in U.S. Pat. No. 5,869,701; quinolones, as disclosed in U.S. Pat. No. 5,955,256; free radical and reactive forms of oxygen, as disclosed in U.S. Pat. Nos. 5,981,163 and 6,087,141; and phenothiazin-5-ium dyes, as disclosed in U.S. Pat. No. 6,030,767. U.S. Pat. No. 6,106,773 discloses another method for disinfecting biological fluids, including platelets, by contacting the biological fluids with an iodinated matrix material.

These sterilization methods, however, do not extend storage life of platelet but, on the contrary, appear to result in the significant loss of platelet function and reduction in the in vivo CCI (corrected count increment) and circulating half life by activating platelets. To effectively extend the shelf life of platelets, not only are sterilization methods for preventing contamination of the platelets important, but it also would be beneficial to provide improved methods to protect the platelets during the sterilization. It would also be beneficial to provide a convenient, effective platelet preservation composition for prolonging the shelf-life of the platelets, while maintaining the functionality and freshness of the platelets. In addition, it would be beneficial to provide a method or composition for storing platelets that requires less management of the surrounding platelet storage environment.

SUMMARY

One aspect of the present invention relates to a platelet preservation composition that preserves the freshness and shelf-life of stored platelets. In one embodiment, the platelet preservation composition comprises a photosensitizer, a platelet activation inhibitor and an anticoagulant. In other embodiments, the platelet preservation composition further comprises one or more preservative agents, such as non-steroidal anti-inflammatory drugs, oxygen carriers, and antimicrobial agents. The preservation composition allows inactivation of pathogens in a platelet preparation while maintaining the functionality of the platelets.

Another aspect of the present invention relates to a preserved platelet composition, comprising platelets, an effective amount of a photosensitizer, and an effective amount of one or more platelet preservation agents comprising a platelet activation inhibitor and/or an anticoagulant, wherein the preserved platelet composition is sterilized by exposure to a radiation at a wavelength that sensitizes the photosensitizer and wherein the platelet composition is substantially free of red blood cells or other blood nutrients.

Another aspect of the present invention relates to a method of extending the shelf-life of platelets. In one embodiment, the method comprises (a) admixing a platelet composition with an effective amount of a photosensitizer to form a platelet mixture; and (b) irradiating the platelet mixture with light under conditions sufficient to sensitize the photosensitizer and inactivate pathogens in the platelet mixture, wherein an effective amount of a platelet activation inhibitor and/or an effective amount of an anticoagulant are added to the platelet composition either before or immediately after step (b).

BRIEF DESCRIPTION OF FIGURES

The file of this patent contains at least one drawing executed in color. Copies of this patent with color drawings will be provided by the Patent and Trademark Office upon request and payment of the necessary fee.

FIG. 2A shows HPLC traces of argatroban samples after various exposures to UV (trace A-F), the positive control (unexposed 50 µg/mL Argatroban) and a the negative control (saline blank). FIG. 2B is a graphical representation of the loss in peak height associated with the exposure to $UV_{282}$, expressed as % relative to the positive control with standard deviations shown.

FIG. 3A shows HPLC traces of argatroban samples after various exposures to UV (trace A-F), the positive control (unexposed 50 µg/mL Argatroban) and a the negative control (saline blank). FIG. 3B is a graphical representation of the loss in peak height associated with the exposure to $UV_{308}$, expressed as % relative to the positive control with standard deviations shown.

FIG. 5A shows HPLC traces of tirofiban samples after various exposures to UV (trace A-F), the positive control (unexposed 50 µg/mL Argatroban) and a the negative control (saline blank). FIG. 5B is a graphical representation of the loss in peak height associated with the exposure to $UV_{282}$, expressed as % relative to the positive control with standard deviations shown. Traces E and F were below the lower limits of quantitation (LLOQ) for the assay.

FIG. 6A shows HPLC traces of tirofiban samples after various exposures to UV (trace A-C), the positive control (unexposed 50 µg/mL Argatroban) and a the negative control (saline blank). FIG. 6B is a graphical representation of the loss in peak height associated with exposure to $UV_{308}$, expressed as % relative to control with standard deviations shown.

FIG. 7A shows HPLC traces of eptifibatide samples after various exposures to UV (trace A-F), the positive control (unexposed 50 Argatroban) and a the negative control (saline blank). FIG. 7B is a graphical representation of the loss in peak height associated with the exposure to $UV_{308}$, expressed as % relative to control with standard deviations shown.

FIG. 8A shows HPLC traces of eptifibatide samples after various exposures to UV (trace A-F), the positive control (unexposed 50 µg/mL Argatroban) and the negative control (saline blank). FIG. 8B is a graphical representation of the loss in peak height associated with the exposure to $UV_{308}$, expressed as % relative to control and with standard deviations shown.

DETAILED DESCRIPTION

Figure 1:
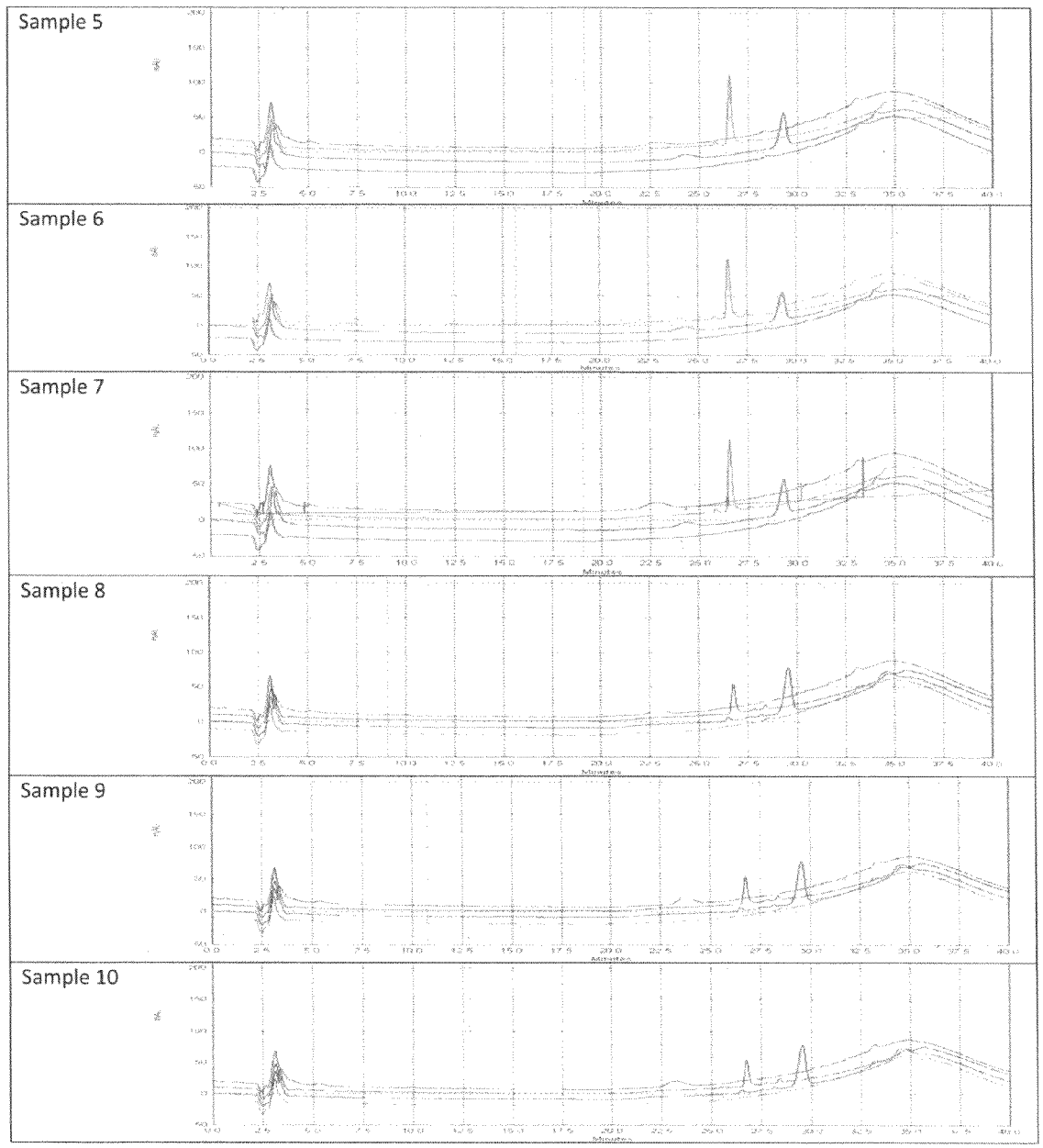
FIG. 1 shows representative chromatograms from samples after diafiltration. The four traces in each chromatogram are: bottom trace—blank control; $2^{nd}$ trace from bottom—5 µg/mL argatroban control; $3^{rd}$ trace from bottom—0.25 µg/mL eptifibatide control (samples 5-7) or 0.25 µg/mL tirofiban control (samples 8-10); top trace—diafiltered samples, samples 5-7 were spiked with either 0.1 µg/mL tirofiban and 8 µg/mL argatroban before diafiltration, samples 8-10 were spiked with 0.1 µg/mL tirofiban and 8 µg/mL argatroban before diafiltration.

The following detailed description is presented to enable any person skilled in the art to make and use the invention. For purposes of explanation, specific nomenclature is set forth to provide a thorough understanding of the present invention. However, it will be apparent to one skilled in the art that these specific details are not required to practice the invention. Descriptions of specific applications are provided only as representative examples. Various modifications to the preferred embodiments will be readily apparent to one skilled in the art, and the general principles defined herein may be applied to other embodiments and applications without departing from the scope of the invention. The present invention is not intended to be limited to the embodiments shown, but is to be accorded the widest possible scope consistent with the principles and features disclosed herein.

Preservation Composition

One aspect of the present invention relates to a preservation composition that preserves the freshness of platelets and/or extends the shelf-life of donated platelets. In one embodiment, the preservation composition comprises a photosensitizer and one or more preservative agents. Exemplary preservative agents include, but are not limited to, platelet activation inhibitors, anticoagulants, oxygen carriers, non-steroidal anti-inflammatory drugs, and anti-microbial agents.

In a particular embodiment, the preservation composition comprises a photosensitizer, a platelet activation inhibitor and/or an anticoagulant. The photosensitizer is used in a photoradiation pathogen inactivation process to improve pathogen killing and platelet quality. The platelet activation inhibitors and/or anticoagulants prevent or reduce activation of platelets during the pathogen inactivation process.

In another embodiment, the preservation composition comprises a photosensitizer, a platelet activation inhibitor and/or an anticoagulant, and an oxygen carrier.

Photosensitizers

In one embodiment, the preservation composition comprises a photosensitizer for pathogen inactivation, a platelet activation inhibitor, and an anticoagulant. The photosensitizer is used in a photoradiation pathogen inactivation process to improve pathogen killing and platelet quality. The platelet activation inhibitors and anticoagulants prevent or reduce activation of platelets during the pathogen inactivation process.

The term "photosensitizer" as used herein refers to a compound which absorbs radiation at one or more defined wavelengths and has the ability to utilize the absorbed energy to carry out a chemical process, such as facilitating the formation of phototoxic species sufficient for killing one or more pathogens. A photosensitizer is "sensitive to" or "sensitized by" radiation at a wavelength if it absorbs the radiation at this wavelength.

Examples of photosensitizer include, but are not limited to, quinoline, quinolones, riboflavin, nitric oxide, pyrrole derived macrocyclic compounds, naturally occurring or synthetic porphyrins and derivatives thereof naturally occurring or synthetic chlorins and derivatives thereof, naturally occurring or synthetic bacteriochlorins and derivatives thereof; naturally occurring or synthetic isobacteriochlorins and derivatives thereof, naturally occurring or synthetic phthalocyanines and derivatives thereof, naturally occurring or synthetic naphthalocyanines and derivatives thereof; naturally occurring or synthetic porphycenes and derivatives thereof; naturally occurring or synthetic porphycyanines and derivatives thereof, naturally occurring or synthetic pentaphyrins and derivatives thereof; naturally occurring or synthetic sapphyrins and derivatives thereof, naturally occurring or synthetic benzochlorins and derivatives thereof; naturally occurring or synthetic chlorophylls and derivatives thereof, naturally occurring or synthetic azaporphyrins and derivatives thereof; the metabolic porphyrinic precursor 5-amino levulinic acid and any naturally occurring or synthetic derivatives thereof, PHOTOFRIN™, synthetic diporphyrins and dichlorins, O-substituted tetraphenyl porphyrins (picket fence porphyrins), 3,1-meso tetrakis (o-propionamido phenyl) porphyrin, verdins, purpuriris (e.g., tin and zinc derivatives of octaethylpurpurin (NT2), and etiopurpurin (ET2)), zinc naphthalocyanines, anthracenediones, anthrapyrazoles, aminoanthraquinone, phenoxazine dyes, chlorins (e.g., chlorin e6, and mono-1-aspartyl derivative of chlorin e6), benzoporphyrin derivatives (BPD) (e.g., benzoporphyrin monoacid derivatives, tetracyanoethylene adducts of benzoporphyrin, dimethyl acetylenedicarboxylate adducts of benzoporphyrin, Diels-Adler adducts, and monoacid ring "a" derivative of benzoporphyrin), low density lipoprotein mediated localization parameters similar to those observed with hematoporphyrin derivative (HPD), sulfonated aluminum phthalocyanine (Pc) (sulfonated AlPc, disulfonated ($AlPcS_2$), tetrasulfonated derivative, sulfonated aluminum naphthalocyanines, chloroaluminum sulfonated phthalocyanine (CASP)), phenothiazine derivatives, chalcogenapyrylium dyes cationic selena and tellurapyrylium derivatives, ring-substituted cationic PC, pheophorbide alpha, hydroporphyrins (e.g., chlorins and bacteriochlorins of the tetra(hydroxyphenyl) porphyrin series), phthalocyanines, hematoporphyrin (BP), protoporphyrin, uroporphyrin III, coproporphyrin III, protoporphyrin IX, 5-amino levulinic acid, pyrromethane boron difluorides, indocyanine green, zinc phthalocyanine, dihematoporphyrin (514 nm), benzoporphyrin derivatives, carotenoporphyrins, hematoporphyrin and porphyrin derivatives, rose bengal (550 nm), bacteriochlorin A (760 nm), epigallocatechin, epicatechin derivatives, hypocrellin B, urocanic acid, indoleacrylic acid, rhodium complexes, etiobenzochlorins, octaethylbenzochlorins, sulfonated Pc-naphthalocyanine, silicon naphthalocyanines, chloroaluminum sulfonated phthalocyanine (610 nm), phthalocyanine derivatives, iminium salt benzochlorins and other iminium salt complexes, Merocyanin 540, Hoechst 33258, and other DNA-binding fluorochromes, psoralens, acridine compounds, suprofen, tiaprofenic acid, non-steroidal anti-inflammatory drugs, methylpheophorbide-a-(hexyl-ether) and other pheophorbides, furocoumarin hydroperoxides, Victoria blue BO, methylene blue, toluidine blue, porphycene compounds as described in U.S. Pat. No. 5,179,120, indocyanines, psoralens, coumarins or other polycyclic ring compounds, as disclosed in U.S. Pat. No. 5,869,701, hypericins, as disclosed in U.S. Pat. No. 6,001,882, free radical and reactive forms of oxygen, as disclosed in U.S. Pat. Nos. 5,981,163 and 6,087,141; phenothiazin-5-ium dyes, as disclosed in U.S. Pat. No. 6,030,767, and combinations of the above. The entire contents of the above-mentioned U.S. patents are herein incorporated by reference.

In one embodiment, the photosensitizer is sensitive to ultraviolet (UV) light. In another embodiment, the photosensitizer is sensitive to non-UV light, including longer wavelengths ranging from about 600 to about 1200 nm. In a related embodiment, a combination of photosensitizers may be utilized, wherein at least one is sensitive to UV light and one is sensitive to non-UV light.

In another embodiment, the photosensitizer is a compound preferentially adsorbing to nucleic acids, such as psoralen, thereby focusing its photodynamic effects upon microorganisms and viruses with little or no effect upon accompanying platelets and other non-nucleated cells or proteins.

The photosensitizer may be an endogenous photosensitizer or a non-endogenous photosensitizer. The term "endogenous" as used herein refers to photosensitizers naturally found in a human or mammalian body, either as a result of synthesis by the body, ingestion (e.g. vitamins), or formation of metabolites and/or byproducts in vivo. Exemplary endogenous photosensitizers include, but are not limited to, alloxazines, such as 7,8-dimethyl-10-ribityl isoalloxazine (riboflavin or vitamin B2), 7,8,10-trimethylisoalloxazine (lumiflavin), 7,8-dimethylalloxazine (lumichrome), isoalloxazine-adenine dinucleotide (flavine adenine dinucleotide [FAD]), alloxazine mononucleotide (also known as flavine mononucleotide [FMN] and riboflavine-5-phosphate), vitamin Ks, including vitamin K1, vitamin K1 oxide, vitamin vitamin K5, vitamin K-S (II), vitamin K6, vitamin K7, vitamin L, their metabolites and precursors, and napththoquinones, naphthalenes, naphthols and their derivatives having planar molecular conformations. The term "alloxazine" includes isoalloxazines. Endogenously-based derivative photosensitizers include synthetically derived analogs and homologs of endogenous photosensitizers which may have or lack lower (1-5) alkyl or halogen substituents of the photosensitizers from which they are derived, and which preserve the function and substantial non-toxicity thereof.

When endogenous photosensitizers are used, particularly when such photosensitizers are not inherently toxic or do not yield toxic photoproducts after photoradiation, it may be unnecessary to remove the photosensitizer prior to transfusion of the treated platelets. When using photosensitizers that are toxic or yield toxic photoproducts, however, the toxic products may be removed by diafiltration or other suitable removal means, including those as further described below.

In certain embodiments, the photosensitizer is riboflavin. In some embodiments, riboflavin is used in the concentration range of 1-200 µM, 25-150 µM, or 50-100 µM. In other embodiments, the photosensitizer is psoralen. In some embodiments, psoralen is used in the concentration range of 1-200 µM, 25-150 µM, or 50-100 µM. In yet other embodiments, the photosensitizer is methylene blue. In some embodiments, methylene blue is used in the concentration range of 0.2-50 µM, 1-20 µM, or 2.5-10 µM.

The photosensitizer is added in an amount sufficient to produce phototoxic species killing one or more pathogens. The effective concentration varies for each particular photosensitizer. There is a reciprocal relationship between photosensitizer compositions and light dose, thus, determination of effective concentration, suitable wavelength, light intensity, and duration of illumination is within ordinary skill in the art.

The photosensitizer is added in an amount sufficient for inactivating one or more blood-borne pathogens, preferably all blood-borne pathogens, but less than a toxic (to humans or other mammals) or insoluble amount. Preferably, the photosensitizer is used in a concentration of at least about 1 µM up to the solubility of the photosensitizer in the fluid medium. There is a reciprocal relationship between photosensitizer compositions and light dose, thus, determination of effective concentration, suitable wavelength, light intensity, and duration of illumination is within ordinary skill in the art.

Platelet preservation compositions and preserved platelet compositions of the present invention may be stored in a range of temperatures between about −80° C. to about 42° C. As used herein, the term "room temperature" or "ambient temperature" refers to a temperature in the range of 12° C. to 30° C.; the term "body temperature" refers to a temperature in the range of 35° C. to 42° C.; the term "refrigeration temperature" refers to a temperature in the range of 0° C. to 12° C.; and the term "freezing temperature" refers to a temperature below 0° C. The term "cold storage" or "storage at low temperature" refers to storage at −20° C. to 12° C., preferably 2° C. to 12° C., more preferably 4° C. to 8° C.

Platelet Activation Inhibitors

Platelet activation inhibitors include any agent that reversibly impedes platelet activation and/or aggregation by blocking sites on the platelet surface can be used as the antiplatelet agent in the present invention. Platelet activation inhibitors include, but are not limited to, GPIIb/IIIa antagonists including bifunctional inhibitors of both GPIIb and IIIa, thrombin antagonists, P2Y12 receptor antagonists, and second messenger effectors.

In certain embodiments, the GPIIb/IIIa antagonists are GPIIb/IIIa antagonists that bind GPIIb/IIIa sites in a reversible manner. As used herein, the term "reversible" or "reversibly" refers to an act, such as binding or associating, that is capable of reverting back to an original condition prior to the act, for example the state of being unbound or disassociated, either with or without the assistance of an additional constituent. Examples of such GPIIb/IIIa antagonists include Eptifibatide (INTEGRILIN®, Schering-Plough Corporation, Kenilworth, N.J., U.S.A.), Orbofiban, Xemilofiban, Lamifiban, Tirofiban (AGGRASTAT®), Abciximab (REOPRO®), Lefradafiban, Sibrafiban and Lotrafiban. In one embodiment, the GPIIb/IIIa antagonists are bifunctional inhibitors of both GPIIb/IIIa as described in U.S. Pat. No. 5,242,810, which is incorporated herein by reference.

In another embodiment, the platelet activation inhibitors include one or more thrombin antagonists. These agents interact with thrombin and block its catalytic activity on fibrinogen, platelets and other substrates. Heparin and its derivatives (low molecular weight heparins and the active pentasaccharide) inhibit thrombin and/or other coagulation serine proteases indirectly via antithrombin, and the warfarin-type drugs interfere with the synthesis of the precursors of the coagulation serine proteases. The direct thrombin inhibitors approved for clinical use at present (Lepirudin, Desirudin, Bivalirudin, Argatroban) and another in the advanced clinical testing stage (Melagatran/Xirnelagatran).

In another embodiment, the platelet activation inhibitors include one or more P2Y12 receptor antagonists. Examples of P2Y12 receptor antagonists include, but are not limited to, prasugrel, cungrelor and AZD6140.

In another embodiment, the platelet activation inhibitors include one or more second messenger effectors. Second messenger effectors include any agent inhibiting a chemical pathway in a platelet so as to reduce platelet activation. Examples of second messenger effectors include, but are not limited to, "Thrombosol" (Life Cell Corp), linear or novel cyclic RGD peptide analogs, cyclic peptides, peptidomimetics, non-peptide analogs conjugated to nitric oxide donor, and the like, and mixtures thereof.

Second messenger effectors also include calcium sequestering agents, such as calcium channel blockers, α-blockers, β-adrenergic blockers and mixtures thereof. More specific examples of calcium sequestering agents include, but are not limited to, anticoagulant citrate dextrose solution, anticoagulant citrate dextrose solution modified, anticoagulant citrate phosphate dextrose solution, anticoagulant sodium citrate solution, anticoagulant citrate phosphate dextrose adenine solution, potassium oxalate, sodium citrate, sodium oxalate, amlodipine, bepridil hydrochloride, diltiazem hydrochloride, felodipine, isradipine, nicardipine hydrochloride, nifedipine, nimodipine, verapamil hydrochloride, doxazocin mesylate, phenoxybenzamine hydrochloride, phentolamine mesylate, prazosin hydrochloride, terazosin hydrochloride, tolazoline hydrochloride, acebutolol hydrochloride, atenolol, betaxolol hydrochloride, bisoprolol fumarate, carteolol hydrochloride, esmolol hydrochloride, indoramine hydrochloride, labetalol hydrochloride, levobunolol hydrochloride, metipranolol hydrochloride, metoprolol tartrate, nadolol, penbutolol sulfate, pindolol, propranolol hydrochloride, terazosin hydrochloride, timolol maleate, guanadrel sulfate, guanethidine monosulfate, metyrosine, reserpine and mixtures thereof.

In a preferred embodiment, the platelet activation inhibitor has short-to-ultra short half-life. By short-to-ultra short half life is meant that the platelet activation inhibitor is cleared from circulation within 15 minutes to 8 hours, preferably within 4 hours or less, after the infusion of the antiplatelet agent into the patient is stopped.

In one embodiment, the platelet activation inhibitor is an active agent that binds to or associates with the GPIIb/IIIa sites in a reversible manner and has a circulating half-life of inhibition of 4 hours or less. Short to ultra-short acting GPIIb/IIIa antagonist might include Eptifibatide (INTEGRILIN®), Tirofiban (AGGRASTAT®), Abciximab (REOPRO®), Lefradafiban, Sibrafiban, Orbofiban, Xemilofiban, Lotrafiban, XJ757, and XR299 (Class II).

In one embodiment, the preservation composition includes Eptifibatide. In another embodiment, the Eptifibatide is present in the composition at a final concentration of about 5-500 μg per unit of platelets. In another embodiment, the platelet activation inhibitor is Eptifibatide at a final concentration of about 50 μg per unit of platelets. Typically, a unit of platelets obtained by the buffy coat method contains about $3 \times 10^{11}$ platelets in approximately 300 ml of plasma or other suitable preservation composition. A unit of platelets collected by apheresis usually contain $5 \times 10^9$ platelets in 250 ml of plasma or other suitable fluid. In another embodiment, the platelet activation inhibitor is present in the composition at a final concentration that is 2-3 times of the therapeutic concentration. The term "therapeutic concentration" refers to the inhibitor concentration that is commonly used in the field for platelet preservation.

Anticoagulants

In another embodiment, the preservation composition further comprises one or more anticoagulants. Examples of anticoagulants include, but are not limited to, heparin, heparin substitutes, prothrombopenic anticoagulants, platelet phosphodiesterase inhibitors, dextrans, thrombin antagonists, and mixtures thereof.

Examples of heparin and heparin substitutes include, but are not limited to, heparin calcium, such as calciparin; heparin low-molecular weight, such as enoxaparin and lovenox; heparin sodium, such as heparin, lipo-hepin, liquaemin sodium, and panheprin; and heparin sodium dihydroergotamine mesylate.

Suitable prothrombopenic anticoagulants are, for example, anisindione, dicumarol, warfarin sodium, and the like. More specific examples of phosphodiesterase inhibitors suitable for use in the invention include, but are not limited to, anagrelide, dipyridamole, pentoxifyllin, and theophylline. Examples of dextrans include, for example, dextran 70, such as HYSKON® (CooperSurgical, Inc., Shelton, Conn., U.S.A.) and MACRODEX® (Pharmalink, Inc., Upplands Vasby, Sweden), and dextran 75, such as GENTRAN® 75 (Baxter Healthcare Corporation, Deerfield, Ill., U.S.A.).

The anticoagulants may also include Xa inhibitors, IIa inhibitors, and mixtures thereof. Various direct Xa inhibitors were synthesized and advanced to clinical development (Phase I-II) for the prevention and treatment of venous thromboembolic disorders and certain settings of arterial thrombosis [Hirsh and Weitz, *Lancet,* 93:203-241, (1999); Nagahara et al., *Drugs of the Future,* 20: 564-566, (1995); Pinto et al., 44: 566-578, (2001); Pruitt et al., *Biorg. Med. Chem. Lett.,* 10: 685-689, (2000); Quan et al., *J Med. Chem.* 42: 2752-2759, (1999); Sato et al., *Eur. J. Pharmacol.,* 347: 231-236, (1998);

Wong et al, *J. Pharmacol. Exp. Therapy*, 292:351-357, (2000)]. A direct anti-IIa (thrombin) such as melagatran, the active form of pro-drug ximelagatran [Hirsh and Weitz, *Lancet*, 93:203-241, (1999); Fareed et al., *Current Opinion in Cardiovascular, pulmonary and renal investigational drugs*, 1:40-55, (1999)].

In certain embodiments, the anticoagulant is a short-to-ultra short acting anticoagulant. By short or ultra short half life is meant that the anticoagulant is cleared from circulation within 15 minutes to 8 hours after the infusion of the anticoagulant into the patient is stopped. In one embodiment, the short-to-ultra short acting anticoagulant is a short-to-ultra short acting factor Xa inhibitor with a circulating half-life of less than 4 hours. Examples of ultra-short acting factor Xa inhibitors include, but are not limited to, DX-9065a, RPR-120844, BX-807834 and SEL series Xa inhibitors DX-9065a is a synthetic, non-peptide, propanoic acid derivative, 571D selective factor Xa inhibitor (Dai chi). It directly inhibits factor Xa in a competitive manner with an inhibition constant in the nanomolar range (Herbert et al., *J. Pharmacol. Exp. Ther.* 276:1030-1038 (1996); Nagahara et al., *Eur. J. Med. Chem.* 30(suppl):140s-143s (1995)).

As a non-peptide, synthetic factor Xa inhibitor, RPR-120844 (Rhone-Poulenc Rorer), is one of a series of novel inhibitors which incorporate 3-(S)-amino-2-pyrrolidinone as a central template (Ewing et al., *Drugs of Future* 24(7):771-787 (1999)). This compound has a Ki of 7 nM with selectivity >150-fold over thrombin, activated protein C, plasmin and t-PA. It prolongs the PT and αPTT in a concentration-dependent manner, being more sensitive to the αPTT. It is a fast binding, reversible and competitive inhibitor of factor Xa.

BX-807834 has a molecular weight of 527 Da and a Ki of 110 μM for factor Xa as compared to 180 μM for TAP and 40 nM for DX-9065a (Baum et al., *Circulation*. 98 (17), Suppl 1: 179, (1998)).

The SEL series of novel factor Xa inhibitors (SEL-1915, SEL-2219, SEL-2489, SEL-2711: Selectide) are pentapeptides based on L-amino acids produced by combinatorial chemistry. They are highly selective for factor Xa and potency in the pM range. The Ki for SEL 2711, one of the most potent analogues, is 0.003 M for factor Xa and 40 M for thrombin (Ostrem et al., *Thromb. Haemost.* 73:1306 (1995); Al-Obeidi and Ostrem., *Exp. Opin. Ther. Patents* 9(7):931-953 (1999)).

In another embodiment, the short-to-ultra short acting anticoagulant is a short-to-ultra short acting factor IIa inhibitor. Examples of short-to-ultra short acting anticoagulant include, but are not limited to, DUP714, hirulog, hirudin, melgatran and combinations thereof. In another embodiment, the anticoagulant is present in the composition at a final concentration that is 2-3 times of the therapeutic concentration. The term "therapeutic concentration" refers to the anticoagulant concentration that is commonly used in the field for platelet preservation.

Oxygen Carriers

The preservation composition may further comprise a pharmaceutically acceptable oxygen carrier. The oxygen carrier can be any suitable red blood cell substitute. In a preferred embodiment, the oxygen carrier is a hemoglobin-based oxygen carrier. Still more preferably, the oxygen carrier is an acellular hemoglobin-based oxygen carrier substantially free of red cell membrane (stroma) contaminants.

The use of a hemoglobin-based oxygen carrier, even in small volumes, as part of the platelet preservation composition provides significantly greater concentration of oxygen than amounts currently made available by the use of oxygen-permeable storage bags. Adding an oxygen carrier (e.g., a stroma-free hemoglobin solution) to platelets can allow for the use of gas impermeable bags, which reduces the high cost associated with using gas permeable bags.

The term "pharmaceutically acceptable oxygen carrier" as used herein refers to a substance that has passed the FDA human safety trials at a hemoglobin dosage of 0.5 g/kg body weight or higher. An oxygen carrier suitable for the invention can be hemoglobin, ferroprotoporphyrin, perfluorochemicals (PFCs), and the like. The hemoglobin can be from human or any other suitable mammalian source. In a preferred embodiment, the preservation composition has a hemoglobin concentration from the range of 1 to 18 gm/dl and a methemoglobin concentration of less than about 5%. The hemoglobin based oxygen carrier can be chemically modified to mimic the oxygen loading and unloading characteristics of fresh red blood cells. Additionally, the chemical modification can enhance the buffering capacity of the preferred embodiment and preserve normal physiologic pH.

Non-Steroidal Anti-Inflammatory Drugs

The preservation composition may further comprise one or more non-steroidal anti-inflammatory drugs (NSAIDS). The NSAIDS suitable for the invention can be salicylate-like or non-salicylate NSAIDS that bind reversibly and inhibit platelet aggregation in vitro, but are cleared rapidly, i.e. quickly eliminated from the body (typically, in less than about 2 hours after infusion). Examples of salicylate-like NSAIDS include, but are not limited to, acetaminophen, carprofen, choline salicylate, magnesium salicylate, salicylamide, sodium salicylate, sodium thiosulfate, and mixtures thereof. Examples of non-salicylate NSAIDS include, but are not limited to, diclofenac sodium, diflunisal, etodolac, fenoprofen calcium, flurbiprofen, hydroxychloroquin, ibuprofen, indomethacin, ketoprofen, ketorolac tromethamine, meclofenamate sodium, mefenamic acid, nabumetone, naproxen, naproxen sodium, oxyphenbutazone, phenylbutazone, piroxicam, sulfinpyrazone, sulindac, tolmetin sodium, dimethyl sulfoxide and mixtures thereof.

Anti-Microbial Agents

The preservation composition may comprise an anti-microbial agent, preferably a short-to-ultra-short acting broad spectrum anti-microbial agent. By short or ultra short acting anti-microbial agent is meant that the agent is cleared from circulation within 15 minutes to 8 hours after the infusion of the antimicrobial into the patient is stopped. Examples of such agents include, but are not limited to, penicillin, monobactam, cephalosporin, carbapenems, vancomycin, isoniazid (INH), ethambutol, aminoglycoside, tetracycline, chloramphenicol, macrolide, rifamycin, quinolone, fluoroquinolone, sulfonamide, polyene antibiotic, triazole, griseofulvin, and derivatives and combinations thereof.

Quenchers

Quenchers may also be added to the preservative composition to make the irradiation process more efficient and selective. Such quenchers include antioxidants or other agents to prevent damage to desired fluid components or to improve the rate of pathogen inactivation and are exemplified by adenine, histidine, cysteine, tyrosine, tryptophan, ascorbate, N-acetyl-L-cysteine, propyl gallate, glutathione, mercaptopropionylglycine, dithiothreotol, nicotinamide, BHT, BHA, lysine, serine, methionine, glucose, mannitol, vitamin E, trolox, alpha-tocopheral acetate and various derivatives, glycerol, and mixtures thereof. Quenchers may be added to the platelet preservation composition in an amount necessary to prevent damage to the platelets.

Other Additives

Other additives, including the glycolytic inhibitor 2-deoxy-D-glucose, may also be used with the platelet preservation composition of this invention. In platelets, 2-deoxy-D-glucose slows down the rate of glycolysis by competing with glucose for enzymes utilized in the glycolysis pathway. 2-deoxy-D-glucose is phosphorylated by the same enzymes which phosphorylate glucose, but at a slower rate than that of glucose phosphorylation. Such competitive binding slows the rate of glucose breakdown by the cell and consequently slows the rate of lactic acid production by platelets during storage. Such an additive may help contribute to platelet viability during and after pathogen inactivation. 2-deoxy-D-glucose may be added to the platelet preservation composition at a concentration of about 10 mM.

Preservative Formulations

The preservation composition of the present invention may be used in an amount from about 60 to about 200 ml for about one unit of platelets (typically about 80 to about 100 ml of platelets). Alternatively, the preservation composition of the present invention may be combined with about one unit of whole blood, typically about one pint, and separated into various components to afford about one-sixth to about one-tenth whole blood unit of treated platelets.

In one embodiment, the preservation composition contains a photosensitizer and an inhibitor of platelet activation dissolved in about 45 to about 55 ml of an oxygen carrier. In a preferred embodiment, the preservation composition comprises Eptifibatide and Argatroban. When used with a unit of whole blood, the inhibitor of platelet activation can also be dissolved in about 45 to about 55 ml of normal saline to preserve the freshness of the platelets without an oxygen carrier.

The amount of the preservative agents present in the preservation composition depends on the type of preservative agent. For example, the amount of the platelet activation inhibitor should be sufficient to reversibly inhibit binding to a ligand or site on the platelet in a manner that is sufficient to inhibit platelet function. For GPIIb/IIIa inhibitors, such as Eptifibatide, suitable amounts in the preservation composition may range from about 0.5 mg to about 3 mg for 50 ml of acellular hemoglobin-based oxygen carrier substantially free of red cell membrane (stroma) contaminants. NSAIDs, for example, ibuprofen, may be preferably present in the preservation composition in an amount from about 20 mg to about 60 mg for each 50 ml of acellular hemoglobin-based oxygen carrier that is substantially free of red cell membrane contaminants.

The use of short-to-ultra-short acting platelet activation inhibitor, and short-to-ultra-short anticoagulant can reduce the potentially adverse effects of any leftover preservative agents in the preserved platelets.

The term "pharmaceutically acceptable" as used herein refers to a substance that complies with the regulations enforced by the FDA regarding the safety of use in a human or animal subject or a substance that has passed FDA human safety trials. The term "pharmaceutically acceptable platelet activation inhibitor", for example, refers to an active agent that prevents, inhibits, or suppresses platelet adherence and/or aggregation, and comports with guidelines for pharmaceutical use as set forth by the FDA.

By using the preservation composition of the invention, platelets can be stored at room temperature or low temperature as further described below. Platelet function also can be better maintained throughout the 5-day storage period mandated by the FDA, or longer.

Preserved Platelet Compositions

Another aspect of the present invention relates to a preserved platelet composition, comprising platelets, an effective amount of a photosensitizer, and an effective amount of one or more platelet preservation agents comprising a platelet activation inhibitor and/or an anticoagulant, wherein the preserved platelet composition is sterilized by exposure to a radiation at a wavelength that sensitizes the photosensitizer and wherein the platelet composition is substantially free of red blood cells or other blood nutrients.

The term "effective amount," as used herein, refers to an amount effective, at dosages and for periods of time necessary, to achieve the desired result, e.g., sufficient to inactivate pathogens in the platelet prepareation, or sufficient to inactivate platelets in a platelet preparation or prevent activation of platelets in a platelet preparation.

In one embodiment, the preserved platelet composition comprises platelets admixed with a preservation composition comprising a photosensitizer and a platelet activation inhibitor. In another embodiment, the preserved platelet composition comprises platelets admixed with a preservation composition comprising a photosensitizer and an anticoagulant. In another embodiment, the preserved platelet composition comprises platelets admixed with a preservation composition comprising a photosensitizer, a platelet activation inhibitor and an anticoagulant.

The preserved platelet composition may include any of the above-described preservation compositions. The photosensitizers and other preservative agents may be removed prior to transfusion in order to reduce any potentially toxic or adverse effects as further described below. Preferably, the platelets are substantially free of activated platelets both prior to and following treatment of the platelet compositions with the photosensitizers and preservative agents of the present invention. Platelet sources and methods of making the same are further described below.

Method for Extending Shelf-Life of Platelets

Another aspect of the present invention relates to a method of extending the shelf-life of platelets using the preservation composition described above. In one embodiment, the method comprises (a) admixing a platelet composition with an effective amount of a photosensitizer to form a platelet mixture; and (b) irradiating the platelet mixture with light under conditions sufficient to sensitize the photosensitizer and inactivate pathogens in the platelet mixture, wherein an effective amount of a platelet activation inhibitor and/or an effective amount of an anticoagulant are added to the platelet composition either before or immediately after step (b).

Prior to the clinical use of the preserved platelets, certain preservative agents, such as platelet activation inhibitors and/or anticoagulants may be removed, thereby eliminating any concerns of the preservative agents adversely effect the activity of the preserved platelets. Any method suitable for removing the preservative agent(s) while not damaging or activating the platelets can be used. Exemplary removal methods include, but are not limited to, filtration, affinity-based isolation, centrifugation, and chromatography, as further described below.

The photosensitizer is added in an amount sufficient to produce phototoxic species killing or inactivating the reproductive ability of one or more pathogens. The effective concentration varies for each particular photosensitizer.

Preferably the photosensitizer is used in a concentration of at least about 1 µM up to the solubility of the photosensitizer in the fluid. In one embodiment, the photosensitizer is riboflavin and is used at a concentration range between about 1 µM and about 160 µM, preferably about 50 µM. In one embodiment, the photosensitizer is added directly to the platelets.

The platelet mixture containing the photosensitizer is exposed to photoradiation of a defined wavelength for a time sufficient to reduce any pathogens which may be contained in the preservation composition. The wavelength used will depend on the type of photosensitizer selected such that the light source may provide light of about 270 nm to about 700 nm. The use of ultraviolet radiation, especially in the UVA range is the generally accepted method because of its ability to damage DNA of the pathogens. It however requires a higher dosage and/or longer exposure. This can adversely effect the blood product. This is especially true for platelets and also other cellular components of blood. Therefore, radiations are preferably in the UVB and UVC ranges.

The light source may be a simple lamp, or may consist of multiple lamps radiating at different wavelengths. The photoradiation source should be capable of delivering from about 0.01 J/cm$^2$ to about 120 J/cm$^2$. The illumination time varies based upon the type of photosensitizer, but is typically in the range of 30 seconds to 30 minutes.

In certain embodiments, the photoradiation source is a monochromatic radiation source having wavelengths in the range of 250 to 308 nm. Exposure of platelets, plasma or other cellular components of blood, in a highly U.V transmissible container, allows exposure to monochromatic radiation between 3 and 10 Joules/cm$^2$, from above and below. This treatment reduces pathogen levels by 4 to 7 logs.

Irradiating the preservation composition in the presence of photosensitizers may cause the degradation of preservative agents, including the platelet activation inhibitors and/or anticoagulants, as further described below. Accordingly, the preservative agents may be added at higher concentrations to compensate for this loss in activity, and e.g., retain inhibitory activity in the preservation composition during and after the irradiation (or illumination) step. Alternatively, or in addition, preservative agents, including platelet activation inhibitors, may be additionally supplemented following the irradiation step. In one embodiment, platelet activation inhibitor(s) are added at 2-3 times their therapeutic concentration or more. By way of example, in one embodiment, Eptifibatide and Argabotran may be added to platelets at three times their therapeutic concentration (i.e., at about 48 µg Eptifibatide and 2.4 mg Argabotran in 350 ml of platelets).

Inhibitors of platelet activation and anticoagulants may be present in the preservation composition (or added thereto) prior to and/or following the illumination step. Additional preservative agents, including oxygen carriers, NSAID drugs, and/or anti-microbial agents may be similarly present in the preservation composition (or added thereto) prior to and/or following the illumination step. Preferably, the admixed platelets are substantially free of activated platelets prior to addition of the inhibitor(s) of platelet activation.

Preservative agents, including inhibitors of platelet activation and anticoagulants may be added to the platelets separately from the photosensitizer or they can be added together.

In one embodiment, the platelets to be decontaminated to which the photosensitizer and the platelet activation inhibitor is flowed past a photoradiation source such that the flow of the material generally provides sufficient turbulence to distribute the photosensitizer and platelet activation inhibitor throughout the fluid to be pathogen reduced. A separate mixing step may optionally be included.

In another embodiment, the preservation composition, including the photosensitizer and the inhibitor(s) of platelet activation are placed in a photopermeable bag container and irradiated in batch mode, preferably while agitating the container to fully distribute the photosensitizer throughout the fluid and expose all the fluid to the radiation. Platelet activation inhibitors may be added to the preservation composition either before irradiation, during irradiation, after irradiation, or combinations thereof.

In one embodiment, the photopermeable container is a bag (such as a blood bag) made of transparent or semitransparent plastic, and the agitating means preferably includes a mechanism for shaking the bag or container in multiple planes. Further, the container or bag may be oxygen-permeable or oxygen-impermeable.

Prior to the clinical use of the preserved platelets, photosensitizers and/or preservative agents, including inhibitors of platelet activation and/or anticoagulants may be removed or inactivated, thereby eliminating any concerns of adverse or toxic effects from the photosensitizers, platelet preservative agents, or other plasma components prior to transfusion.

When endogenous photosensitizers are used, particularly when such photosensitizers are not inherently toxic or do not yield toxic photoproducts after photoradiation, it may be unnecessary to remove the photosensitizer prior to transfusion of the treated platelets. When using photosensitizers that are toxic or yield toxic photoproducts, however, the toxic products may be removed by diafiltration or other suitable removal means, including those as further described below.

Given that preservative agents may be susceptible to degradation following irradiation, an additional irradiation step may be employed immediately prior to transfusion to inactivate the preservation agents, such as inhibitors of platelet activation and/or anticoagulants. In one embodiment, freshly prepared photosensitizer(s), preferably endogenous photosensitizer(s), is added to the platelet mixture just prior to irradiation for this purpose. Depending on the selection of the preservative agents, this additional irradiation step may provide an alternative to other removal means, including diafiltration as further described below.

Platelet Formulations and Sources

Platelets may be derived from whole blood or platelet-containing components of whole blood, or they may be further isolated therefrom. Preferably, the platelets are substantially free of red blood cells and other blood nutrients and/or are substantially free of activated platelets.

Typically, the blood is whole blood isolated from a mammal, for use in the same species. In the case of a human, the blood is isolated and separated into the three core components of whole blood, i.e., plasma, cells, and platelets. The whole blood, or only the platelet component of the whole blood, can be treated with the preservation composition. If whole blood is treated, a preferred embodiment contemplates the use of only some components of the proposed preservation composition, such as the antiplatelet agent and anticoagulant, for whole blood storage. The blood can then be fractionated and the platelet component can be further mixed with the preservation composition of the present invention for storage.

In one embodiment, platelets are derived from a non-plasma blood component. More particularly, blood is passed through a filter comprising a filtering membrane to separate plasma in blood from the non-plasma component by tangential flow filtration, wherein a diafiltration solution is added to the non-plasma blood component to replace some or all of the permeate volume. The diafiltration solution can be a plasma-free solution commonly used for the storage of the non-plasma blood component but without any antiplatelet agent and/or anticoagulant. Examples of the diafiltration solution include, but are not limited to, Intersol (Fenwal), T-Sol, PAS II, PAS IIIM, PAS27 (Baxter). In one embodiment, the diafiltration buffer is a commercially available platelet storage solution (T-Sol) with 20% to 30% plasma. In one embodiment, an extraction liquid is circulated outside the filtering tube in a counter current manner to facilitate the filtration process. In a related embodiment, the extraction fluid comprises 0.9% w/v sodium chloride.

Upon addition to the preservation composition, the preserved platelets can be stored at room temperature, at refrigeration temperatures (0 C-12 C) or at freezing temperatures (−80 C-0 C) in liquid, frozen, or freeze-dried state to maintain the freshness and functional activity of the platelets. If the platelets will be subsequently frozen or freeze dried, the platelets can be mixed with the preservation composition before freezing.

In one embodiment, the irradiated mixture is stored at 4 C to 12 C. In another embodiment, the irradiated mixture is stored at 4 C to 8 C. In yet another embodiment, the platelet mixture is stored at room temperature.

The platelets may be stored for a desired period of time. In certain embodiments, the desired period of time is one, two, three or four weeks, preferably at ambient temperature. Platelet functional activities may be determined by their ability to aggregate in the presence of certain biological agents and their morphology. Platelet function also can be assessed by the maintenance of the pH upon limited storage of a solution containing the platelets and in vivo haemostatic effectiveness using the rabbit kidney injury model described in Krishnamurti et al., Transfusion, 39:967 (1999). Structural integrity of platelets is assessed by in vivo survival following radiolabeling with carbon-15 or indium-111 and identification of the presence of specific platelet antigens.

The platelets may be isolated from the whole blood using methods commonly used in the art. In one embodiment, a unit of whole blood is centrifuged using settings that precipitate only the cellular components of the blood (e.g., red blood cells and white blood cells). At these settings, the platelets remain suspended in the plasma. The platelet-rich plasma (PRP) is removed from the precipitated blood cells, then centrifuged at a faster setting to harvest the platelets from the plasma.

In another embodiment, the whole blood is centrifuged using settings that cause the platelets to become suspended in the "buffy coat" layer, which includes the platelets and the white blood cells. The "buffy coat" is isolated in a sterile bag, suspended in a small amount of red blood cells and plasma, then centrifuged again to separate the platelets and plasma from the red and white blood cells.

In another embodiment, apheresis platelets are collected using a mechanical device that draws blood from the donor and centrifuges the collected blood to separate out the platelets and other components to be collected. The remaining blood is returned to the donor.

Removal or Inactivation of Photosensitizers and/or Preservative Agents

Prior to the clinical use of the preserved platelets, photosensitizers and/or preservative agents, including inhibitors of platelet activation, serum antibodies, and the like, may be removed or inactivated, thereby eliminating any concerns of adverse effects from the platelet preservative agents or other plasma components prior to transfusion. The use of short to ultra-short acting preservative agents, such as antiplatelet or anticoagulant inhibitors, can further reduce the potentially adverse effects of any leftover preservative agents in the preserved platelets, with or without subsequent removal of these preservative agents.

Any method that is capable of removing or inactivating photosensitizers, preservative agents, or undesirable plasma components while not damaging or activating the platelets can be used. Exemplary removal methods include, but are not limited to, filtration, affinity-based isolation, centrifugation and chromatography. The process of removing these agents can have the additional benefit of removing potentially dangerous plasma components, including those associated with transfusion related acute lung injury. This is particularly the case when using diafiltration as further described below. Exemplary inactivation methods include the use of ultraviolet radiation.

Filtration is a pressure driven separation process that uses membranes (or filters) to separate components in a liquid solution or suspension based on their size differences. Filtration can be broken down into two different operational modes-normal flow filtration (NFF) and tangential flow filtration (TFF). In NFF, fluid is connected directly toward the membrane under an applied pressure. Particulates that are too large to pass through the pores of the membrane accumulate at the membrane surface or in the depth of the filtration media, while smaller molecules pass through to the downstream side. This type of process is also called dead-end filtration.

In TFF, the fluid is pumped tangentially along the surface of the membrane. An applied pressure serves to force a portion of the fluid through the membrane to the filtrate side. As in NFF, particulates and macromolecules that are too large to pass through the membrane pores are retained on the upstream side. However, in this case the retained components do not build up at the surface of the membrane. Instead, they are swept along by the tangential flow. This feature of TFF makes it an ideal process for finer sized-based separations. TFF is also commonly called cross-flow filtration. However, the term "tangential" is descriptive of the direction of fluid flow relative to the membrane.

In one embodiment, the photosensitizers, platelet activation inhibitors, anticoagulants, and/or plasma components are separated from the platelet preparation by diafiltration, wherein a diafiltration buffer is added to the platelet preparation during circulation to maintain a constant volume of the platelet preparation. In a preferred embodiment, the photosensitizers, platelet activation inhibitors, anticoagulants, and/or plasma components are removed by diafiltration with 4-6 volume exchange with an inhibitor-free platelet preservation composition containing 20-30% plasma.

Diafiltration is a TFF method of "washing" or removing permeable molecules (impurities, salts, solvents, small proteins, etc) from a solution, including antibodies from plasma which are associated with transfusion related acute lung injury. Because it is a significantly faster and scalable method, diafiltration frequently replaces membrane tube dialysis. The success of diafiltration is largely determined by the selection of an appropriate membrane. The membrane pores must be large enough to allow the permeable species to pass through and small enough to retain the larger species. A rule of thumb in selecting the membrane is to choose a membrane whose pore size is rated 2-5 times smaller than anything to be retained, and 2-5 times larger than anything to be removed by the filtration. A large variety of pore sizes are available in the ultrafiltration and micro filtration range for this purpose.

In one embodiment, an extraction liquid is circulated outside the filtering tube in a counter current manner to facilitate the filtration process. In a related embodiment, the extraction fluid comprises 0.9% w/v sodium chloride.

In one embodiment, a typical continuous diafiltration system in which the buffer is automatically added to the process reservoir by vacuum suction. It includes a pump, pressure measurement device, flow measurement device, process reservoir, buffer reservoir, and hollow fiber filter module. The pump circulates the process solution from the process reservoir, through the filter and back to the process vessel at a controlled flow and shear rate. Pressure measurements are acquired in this re-circulation loop to control and record the driving force through the membrane. Careful measurement of the permeate flow rate enables accurate process scale up and process optimization. Diafiltration occurs simply by adding the diafiltration buffer to this circulation loop. Working with a hollow fiber module, tubing and an air-tight sealable bottle is a simple means of performing a continuous diafiltration.

To begin the diafiltration in an airtight system, a vacuum needs to be created in the process vessel. This can be accomplished by submerging the buffer addition tube into a bottle of diafiltration buffer. As permeate flows out of the system, the vacuum in the sealed process reservoir pulls buffer into it at a flow rate equal to the process flux. When the target volume of diafiltration buffer has been collected in the permeate vessel, the process is stopped simply by stopping the permeate flow and breaking the vacuum seal on the feed reservoir.

When airtight systems are not possible, particularly for pilot and manufacturing scale processes, buffer addition can be controlled to match the permeate flow rate through the use of a single- or double-headed secondary pump adding buffer into the feed or process reservoir. Sometimes, it is advantageous to reduce the process volume by concentration before diafiltration. There is a relationship between the volume of buffer required to remove a permeable species and the product solution volume in the process reservoir. By understanding this relationship, the cost associated with the process time and the volume of buffer can be minimized.

In a preferred embodiment, the removal of the photosensitizers, platelet activation inhibitors, anticoagulants, and/or plasma components involve the use of tangential flow filtration using micro filtration membranes. Microfiltration membrane materials include, but are not limited to, regenerated cellulose, cellulose acetate, polyamide, polyurethane, polypropylene, polysulfone, polyethersulfone, polycarbonate, nylon, polyimide and combinations thereof. In one embodiment, the microfiltration membrane is a hollow fiber membrane made of polysulfone or polyethersulfone. In another embodiment, the filter membrane tubes has inner diameter of 0.5 mm or greater with the membrane pore size of 0.05 micron or larger. In another embodiment, the membrane has a pore size ranging from a molecular weight cut off of 3000 daltons to 0.5 micron.

In other embodiments, these membranes can be chemically modified to provide a greater positive or negative charge depending on the specific application thereby selectively binding a solute of interest. Alternatively, the surface chemistry of these membranes can be modified to specifically bind solutes of interest such as the antiplatelet agents or direct thrombin inhibitors.

In another embodiment, the platelet preparation is passed through the hollow fiber membrane filter at flow rates ranging from 150 ml/minute to 370 ml/minute. Theses flow rates provide acceptable shear forces from 2000-s to 4000-s. An acceptable pump provides a wide range of flow rates and also provides continuous monitoring of inlet, retentate, permeate and transmembrane pressures. In one embodiment, the pump is the Kros Flow II pump (Spectrum Labs, Rancho Dominguez, Calif.). A replacement fluid suitable for the removal of antiplatelet and anticoagulant agents would be fluids that are used for the storage of platelets. Typically a 10 to 15 volume exchange will result in the removal of better than 99% of the added agents. Typically, 45 to 100 µg of antiplatelet agent, such as Eptifibatide, and 2.5 to 10 mg of anticoagulant, such as argatroban, may be removed from a unit of platelets. Typically, a unit of platelets obtained by the buffy coat method would contain $3 \times 10^{11}$ platelets in approximately 300 ml of plasma or other suitable preservation composition. A unit of platelets collected by apheresis usually contain $5 \times 10^9$ platelets in 250 ml of plasma or other suitable fluid.

In another embodiment, the preserved platelet composition is passed through the hollow fiber filter in a diafiltration device at flow rates ranging from 20 to 400 ml/min, preferably 150 to 400 ml/min. The hollow fiber membrane filters with a pore size ranging from molecular weight cut off of 3000 daltons to 0.5 micron are acceptable. The preferred pore size is 0.05 micron. For the exchange of one unit of platelets (300 to 400 ml) the preferred surface area of the filtration module is 2500 cm$^2$. This setting can allow for the complete removal (>99%) of the photosensitizers, platelet activation inhibitors, anticoagulants, and/or plasma components contained in a unit of platelets in 15 minutes with a flow rate of 370 ml/min. The diafiltration buffer (i.e., replacement fluid) can be any solution suitable for platelet storage. In one embodiment, the diafiltration buffer is a commercially available platelet storage solution (T-Sol) with 20% plasma.

In affinity-based isolation, the photosensitizers, platelet activation inhibitors, anticoagulants, and/or plasma components are removed from a platelet preparation by passing the platelet preparation through the surface of a material that binds specifically to the antiplatelet agent and anticoagulant. The affinity can be based on biological interactions such as antibody-antigen interaction and ligand-receptor interaction, chemical interaction such as hydrophilicity or hydrophobicity based interaction, and electrical interaction such as charge-based interactions. Methods of affinity based-isolation are well known in the art. In one embodiment, the photosensitizers, platelet activation inhibitors, anticoagulants, and/or plasma components are removed from the preserved platelet composition using magnetic beads that specifically bind to these agents.

In one embodiment, the photosensitizers, platelet activation inhibitors, anticoagulants, and/or plasma components are removed from preserved platelet composition by passing the composition through a porous material that specifically binds to one or more of the undesirable agents.

In certain embodiments, the porous material comprises a nanofiber. Examples of nanofiber include, but are not limited to, cellulose nanofibers, biodegradable nanofibers and carbon nanofibers.

Cellulose nanofibers may be obtained from various sources such as flax bast fibers, hemp fibers, kraft pulp, and rutabaga, by chemical treatments followed by innovative mechanical techniques. The nanofibers thus obtained have diameters between 5 and 60 nm. The ultrastructure of cellulose nanofibers is investigated by atomic force microscopy and transmission electron microscopy. The cellulose nanofibers are also characterized in terms of crystallinity. In one embodiment, the membrane filter is a reinforced composite film comprising 90% polyvinyl alcohol and 10% nanofibers.

The chemistry of these cellulose fibers can be modified to provide specific binding sites for a given antiplatelet agent and/or an anticoagulant. These fibers can be coated onto the surface of currently available disposable filter platforms like those used for sterilizing small volumes of fluids.

Biodegradable polymers, such as poly(glycolic acid) (PGA), poly(L-lactic acid) (PLLA) and poly(lactic-co-glycolic acid) (PLGA), can be dissolved individually in the proper solvents and then subjected to electrospinning process to make nanofibrous scaffolds. Their surfaces can then be chemically modified using oxygen plasma treatment and in situ grafting of hydrophilic acrylic acid (AA). In one embodiment, the biodegradable nanofibrous scaffold has a fiber thickness in the range of 200-800 nm, a pore size in the range of 2-30 micron, and porosity in the range of 94-96%.

The ultimate tensile strength of PGA will be about 2.5 MPa on average and that of PLGA and PLLA will be less than 2 MPa. The elongation-at-break will be 100-130% for the three nanofibrous scaffolds. When the surface properties of AA-grafted scaffolds are examined, higher ratios of oxygen to carbon, lower contact angles and the presence of carboxylic (—COOH) groups are identified. With the use of plasma treatment and AA grafting, the hydrophilic functional groups can be successfully adapted on the surface of electrospun nanofibrous scaffolds. These surface-modified scaffolds provide the necessary sites for adding ligands specific to the binding of a given preservative composition agent.

There are several approaches that can be utilized to convert activated carbon into bioreactive fibers. An example is provided to demonstrate the ability of these modified carbon nanofibers to provide carboxylic, hydroxyl and other chemically reactive sites for the binding of any ligand of interest.

Carbon nanofibers (CNF) can be synthesized by chemical vapor deposition (CVD). Amino acids, such as alanine, aspartic acid, glutamic acid and enzymes such as glucose oxidase (GOx) can be adsorbed on CNF. The properties of CNF (hydrophilic or hydrophobic) are characterized by the pH value, the concentration of acidic/basic sites and by naphthalene adsorption. These fibers are readily amenable to crosslinking with ligands of interest, e.g., the ability to selectively bind to antiplatelet agents, anticoagulants, antibodies, etc.

Preserved platelet composition agents may also be removed from a platelet preparation by centrifugation or chromatography. Briefly, platelets may be precipitated under conditions that do not precipitate the antiplatelet agent and anticoagulant. The precipitated platelets are then washed and resuspended for clinical use. Similarly, chromatographic methods such as column chromatography may also be used to separate the platelets from the antiplatelet agent and anticoagulant. Alternatively, the preserved platelet composition agents may be removed from a platelet preparation by affinity-based removal methods such as magnetic beads coated with antibodies that bind to the preserved platelet composition agents.

The foregoing examples illustrate that an acellular platelet preservation composition for freshly collected platelets can be prepared for improving the functional half-life of platelets. The addition of the platelet preservation composition to freshly collected platelets better maintains the original blood clotting function when infused during the storage period of the platelets. The addition of a platelet preservation composition permits an extended storage of the platelets at refrigeration temperatures and allows the platelets to maintain blood clotting properties without affecting the half-life of the platelets in circulation once transfused. As a result, the platelets stored for an extended period can be used for transfusions while saving a substantial amount of effort and cost.

The present invention is further illustrated by the following examples which should not be construed as limiting. The contents of all references, patents and published patent applications cited throughout this application, as well as the Figures and Tables are incorporated herein by reference.

Example 1

General Procedure of Preparing the Preservative Solution

In 50 ml of an acellular chemically modified hemoglobin-based carrier substantially free of red cell membrane (stroma) contaminants, with a hemoglobin concentration of 12-20 gm/dl and a methemoglobin concentration of less than 5%, the following active ingredients are added:

1) a photosensitizer, such as riboflavin, psoralen or methylene blue, in the amount of 1-200 μm (riboflavin or psorale) or 0.2-50 μm (methylene blue), and 2) a platelet activation inhibitor, such as a GPIIb/IIIa antagonist, a thrombin antagonist, a P2Y12 receptor antagonist or a second messenger effector, in an amount of 0.001-5.0 mg.

The above platelet preservation composition is added to the platelets and subjected to a sterilization procedure by exposing to radiation at a desired wave-length. An energy source such as glucose or citrate to sustain aerobic metabolism and electrolytes such as Na, Cl, and Mg, may be added after the sterilization procedure.

TABLE 1 provides the concentration ranges for some commonly used energy sources and electrolytes.

TABLE 1

Commonly Used Energy Sources and Electrolytes

| Component | Concentration (mM) |
|---|---|
| NaCl | 80 to 120 |
| KCl | 5 to 15 |
| $MgCl_2/MgSO_4$ | 2 to 5 |
| $Na_2$ Citrate | 5 to 40 |
| $NaH_2PO_4/Na_2 HPO_4$ | 5 to 30 |
| Na Acetate | 20 to 40 |
| Na Gluconate | 15 to 30 |
| Glucose | 20 to 50 |
| Maltose | 25 to 35 |
| D-Mannitol | 25 to 40 |

Example 2

In Vitro Assessment of Platelet Function and Stability

Cell counts in the platelet concentrates and mea platelet volume were determined electronically using a particle counter. The pH, pO2, pCO2, and bicarbonate levels were determined in a blood gas analyzer. Glucose, lactic acid, and lactic dehydrogenase levels in the platelet concentrates were measured by standard clinical chemistry methodology. Platelet function was measured by aggregometry using ADP and collagen as agonists and by thrombelastography (TEG).

Thrombelastography (TEG)

The principle of TEG is based on the measurement of the physical viscoelastic characteristics of blood clot. Clot formation was monitored at 37° C. in an oscillating plastic cylindrical cuvette ("cup") and a coaxially suspended stationary piston ("pin") with a 1 mm clearance between the surfaces, using a computerized Thrombelastograph (TEG Model 3000, Haemoscope, Skokie, Ill.). The cup oscillates in either direction every 4.5 seconds, with a one second mid-cycle stationary period; resulting in a frequency of 0.1 Hz and a maximal shear rate of 0.1 per second. The pin is suspended by a torsion wire that acts as a torque transducer. With clot formation, fibrin fibrils physically link the cup to the pin and the rotation of the cup as affected by the viscoelasticity of the clot (Transmitted to the pin) is displayed on-line using an IBM-compatible personal computer and customized software (Haemoscope Corp., Skokie, Ill.). The torque experienced by the pin (relative to the cup's oscillation) is plotted as a function of time.

TEG assesses coagulation by measuring various parameters such as the time latency for the initial initiation of the clot (R), the time to initiation of a fixed clot firmness (k) of about 20 mm amplitude, the kinetic of clot development as measured by the angle (a), and the maximum amplitude of the clot (MA). The parameter A measures the width of the tracing at any point of the MA. Amplitude in mm is a function of clot strength or elasticity. The amplitude on the TEG tracing is a measure of the rigidity of the clot; the peak strength or the shear elastic modulus attained by the clot, G, is a function of clot rigidity and can be calculated from the maximal amplitude (MA) of the TEG tracing.

The following parameters were measured from the TEG tracing:

R, the reaction time (gelation time) represents the latent period before the establishment of a 3-dimensional fibrin gel network (with measurable rigidity of about 2 mm amplitude).

Maximum Amplitude (MA, in mm), is the peak rigidity manifested by the clot.

Shear elastic modulus or clot strength (G, dynes/cm2) is defined by: $G=(5000A)/(100-A)$.

Blood clot firmness is important function parameters for in vivo thrombosis and hemostasis because the clot must stand the shear stress at the site of vascular injury. TEG can assess the efficacy of different pharmacological interventions on various factors (coagulation activation, thrombin generation, fibrin formation, platelet activation, platelet-fibrin interaction, and fibrin polymerization) involved in clot formation and retraction.

Blood Sampling

Blood is drawn from consenting volunteers under a protocol approved by the Human Investigations Committee of William Beaumont Hospital. Using the two syringe method, samples are drawn through a 21 gauge butterfly needle and the initial 3 ml blood was discarded. Whole blood (WB) is collected into siliconized Vacutainer tubes (Becton Dickinson, Rutherford, N.J.) containing 3.8% trisodium citrate such that a ratio of citrate whole blood of 1:9 (v/v) is maintained. TEG is performed within 3 hrs of blood collection. Calcium is added back at a final concentration of 1-2.5 mM followed by the addition of the different stimulus. Calcium chloride by itself at the concentration used shows only a minimal effect on clot formation and clot strength.

Statistical Analysis

Data are expressed as mean+SEM. Data are analyzed by either paired or group analysis using Student's t-test or ANOVA when applicable; differences are considered significant at $P<0.05$ or less.

Example 3

Preservative Agent Detection Following Removal by Diafiltration

HPLC-based methods were used to define the performance characteristics for assays to detect levels of Tirofiban (AG-GRASTAT®), Eptifibatide (INTEGRILIN®), and Argatroban following their removal via diafiltration or following their degradation by ultraviolet light treatment.

The removal of the platelet activation inhibitors was accomplished with the use of tangential flow filtration. Platelet concentrates in 100% plasma, containing either Eptifibatide and Argatroban, or Tirofiban and Argatroban, were processed through a hollow fiber filter made of polyethyl sulfone with a pore diameter of 0.5 micron and the inner diameter of the lumen of the filter fiber being 1 mm.

The diafiltration was conducted as a combination of discontinuous and constant volume exchange. Forty milliliter aliquots were processed at a time. A 4 volume discontinuous exchange was done first, which essentially removed most of the plasma proteins. This was followed by a 6 volume constant volume exchange. The flask was sealed. The loss of the permeate was continuously replaced by isotonic saline.

An Agilent XBridge C18 (3.5 µm; 2.1×100 mm) column was used for the method development and sample quantitation experiments below. A flow rate of 0.15 mL/min. was used with Solvent A consisting of Fisher Optima-grade water w/0.1% trifluoroacetic acid (TFA) and Solvent B consisting of Fisher Optima-grade acetonitrile w/0.1% TFA. The gradient sequence is defined in Table 2. Data was recorded at 205 and 230 nm and full spectrum (295-700 nm) by the 168 detector module.

TABLE 2

| (Diafiltration) | | |
| --- | --- | --- |
| Action | Notes | Time (min) |
| Injection (25 µL) | | 0 |
| | 10% B | 0-5 |
| Gradient | 10-70% B | 5-15' |
| | 70-100% B | 15-20' |
| | 100% B | 20-25' |
| | 100-10% B | 25-30' |
| | 10% B | 30-35' |
| Lamp | Stop Run | |

HPLC-based methods were used to define the performance characteristics for assays for detecting Tirofiban, Eptifibatide, and Argatroban following their removal via diafiltration. These methods employed a Beckman-Coulter System Gold HPLC System equipped with a 126 solvent module, a 168 Multiwavelength diode-array detector; and a 508 autosampler module.

Analytical standard curve data for Tirofiban, Eptifibatide, and Argatroban were generated, which allowed for a preliminary assessment of standard assay performance characteristics, including: assay range, reproducibility, lower limit of detection (LLOD), lower limits of quantitation (LLOQ)(data not shown). The standard curve data was generated in a non-serial manner and in duplicate with analytical sampling occurring as single runs. Tirofiban and Eptifibatide were each prepared at 0.1, 0.25, 1, 5, 10, 25, and 50 µg/mL concentrations for assembly of individual standard curves with all dilutions performed in sterile 0.5% saline. Eptifibatide also had 100 and 500 µg/mL concentrations tested. Argatroban was prepared at 5, 25, 100, 500, and 1,000 µg/mL concentrations for standard curve assembly with all dilutions performed in sterile 0.5% saline.

To facilitate quantitation of samples treated by diafiltration, human platelet solutions were spiked either with 0.1 µg/mL Tirofiban and 0.2 µg/mL Eptifibatide or with 0.1 µg/mL Tirofiban and 8 µg/mL Argatroban. Diafiltration that combines a 4 volume discontinuous exchange, followed by a 10 volume constant volume exchange was undertaken, with 7 samples being tested using an Tirofiban/Eptifibatide solution, and 3 samples being tested using Tirofiban/Argatroban solution. All samples were centrifuged at 1,000 g for 15' to remove platelets immediately after diafiltration. The exchange fluid can be physiologic (0.9%) saline or any other approved platelet preservative solution such as Intersol.

The analysis showed that Tirofiban, Eptifibatide, and Argatroban can be removed from a platelet preservation solution below the level of detection in this analytical system. Analysis of samples 1-10 by HPLC was consistent with these results in terms of depletion of the target agents. Representative traces of samples are provided in FIG. 1. Current estimates would place each agent extraction at >99.99% of control.

Example 4

Evaluation of Preservative Agent Photodegradation Upon Exposure to Ultraviolet Light by HPLC Analysis Stability of Tirofiban, Eptifibatide, and Argatroban was evaluated after exposure to ultraviolet radiation. Individual solutions of 5 μg/mL Eptifibatide, 5 μg/mL Tirofiban, and 25 μg/mL Argatroban were prepared for ultraviolet exposure. A total of 6 exposures were performed at 282 nm and 3 exposures at 308 nm, with each exposure being performed in duplicate prior to HPLC analysis. The exposure were varied to provide varying UV dose. This is accomplished by a combination increased intensity and exposure time. A non-exposed control specimen was also processed for each series. Samples were coded for exposure and were analyzed neat using further refined HPLC methods modified as further defined below.

The HPLC analysis was conducted using a Beckman-Coulter System Gold HPLC System equipped with a 126 solvent module, a 168 Multiwavelength diode-array detector; and a 508 autosampler module. A Shimadzu ShimPac ODS (3.5 μm; 2.0×30 mm) column was employed, wherein a flow rate of 0.2 mL/min. was used with Solvent A consisting of Fisher Optima-grade water w/0.1% trifluoroacetic acid (TFA) and Solvent B consisting of Fisher Optima-grade Methanol w/0.1% TFA. The gradient sequence is defined in Tables 3 and 4. All data was recorded at 230 and 280 nm and full spectrum (295-700 nm) by the 168 detector module.

TABLE 3

(Tirofiban and Argatroban)

| Action | Notes | Time (min) |
|---|---|---|
| Injection (25 μL) | | 0 |
| Gradient | 5% B | 0-5 |
| | 5-100% B | 5-10' |
| | 100% B | 10-13' |
| | 100-0% B | 13-16' |
| | 0% B | 16-25' |
| Lamp | Stop Run | |

TABLE 4

(Eptifibatide)

| Action | Notes | Time (min) |
|---|---|---|
| Injection (25 μL) | | 0 |
| Gradient | 5% B | 0-5 |
| | 5-100% B | 5-10' |
| | 100% B | 10-13' |
| | 100-5% B | 13-16' |
| | 5% B | 16-25' |
| Lamp | Stop Run | |

The refined HPLC conditions provided a faster and more reproducible method for these applications, which are readily translatable to LC-MS/MS. Standard curves generated for the three agents tested allowed for a determination of the performance characteristics depicted in Table 5 below:

TABLE 5

Performance characteristics of agents tested with the refined chromatographic conditions.

| | Tirofiban | Argatroban | Eptifibatide |
|---|---|---|---|
| Elution time | 19.3 min | 19.9 min | 17.9 min |
| Range tested | 0.625-20 μg/mL | 1-50 μg/mL | 1.25-10 μg/mL |
| LLOD* | 0.625 μg/mL | 1 μg/mL | 1.25 μg/mL |
| LLOQ* | 2.5 μg/mL | 1 μg/mL | 2.5 μg/mL |
| % CV (curve average) | 0.98 | 1.81 | 9.40 |

*Based on linear fit. A 5-point parametric fit may be able to extend the effective assay range.

Argatroban Exposure to $UV_{282\,nm}$

Figure 2A:
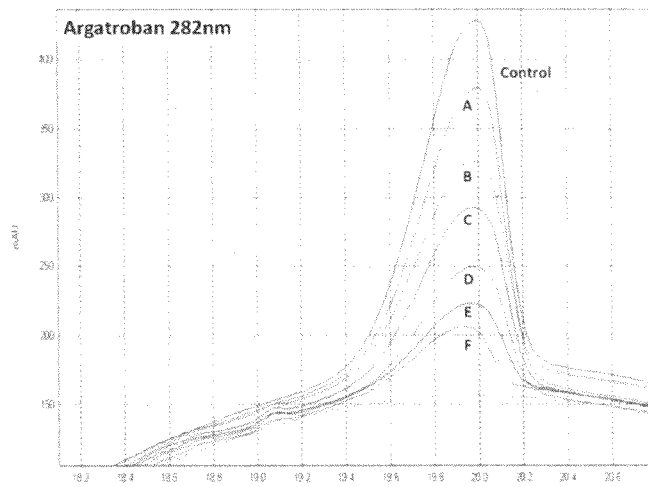
FIGS. 2A and 2B show the photo-degradation profile of argatroban at 282 nm.
Figure 2B:
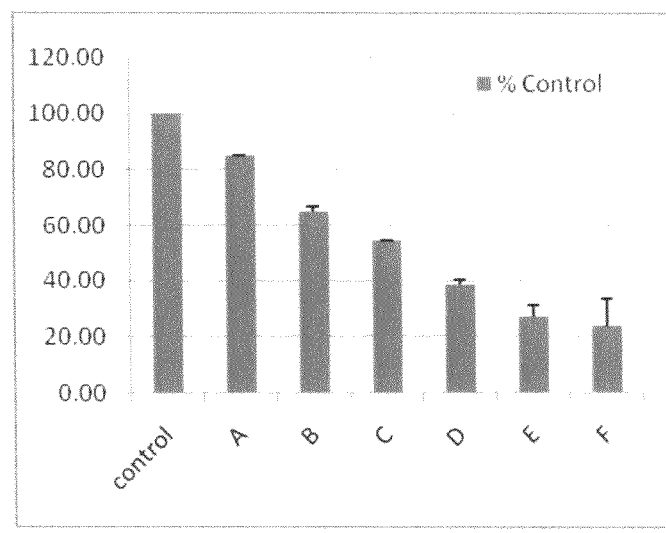

The dose-dependent photodegradation of Argatroban upon exposure to UV light at 282 nm is shown in FIGS. 2A and 2B. FIG. 2A shows HPLC traces of exposures A-F compared to a control (unexposed 50 μg/mL Argatroban) and a saline blank. FIG. 2B (right) is a graphical representation of the loss in peak height associated with the exposure to $UV_{282}$ with standard deviations.

Figure 4:
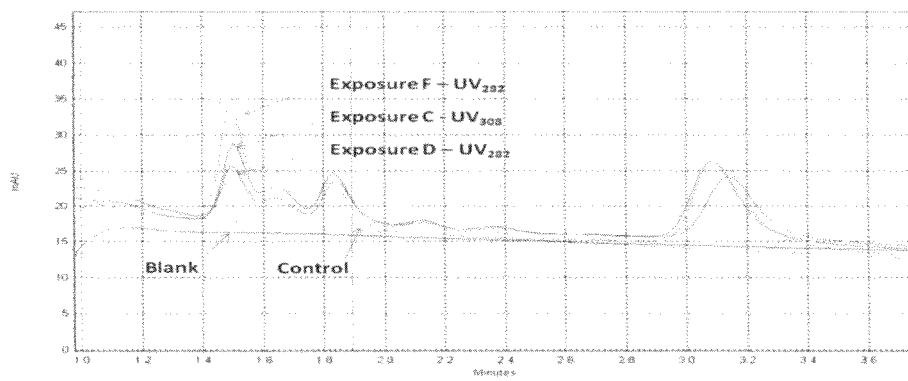
FIG. 4 shows HPLC traces reflecting an identical pattern of photodegradation products at $UV_{282\ nm}$ and $UV_{308\ nm}$ in the two sets of experiments exemplified in FIGS. 2 and 3.

Relative areas were as follows: Control—100%; exposure A—84.5%, exposure B—64.7%, exposure C—53.9%, exposure D—38.1%, exposure E—26.7%, and exposure F—23.2%. Although a steady loss in Argatroban was observed at 19.9 minutes ($A_{230\,nm}$), there was no emergence of a secondary peak in the chromatogram of comparable area to account for discrete photo bleached degradation products. However, a series of species with areas <5% of the original peaks were observed at 18.9', 16.8', 2.83°, and 1.47° were observed, as well as minor species (areas <1% control) at 18.5', 18.2', 17.8', 17.5', 3.15', 2.05°, and 1.77°. FIG. 4 depicts several degradation products associated with the ultraviolet light treatment.

Argatroban Exposure to $UV_{308\,nm}$

Figure 3A:
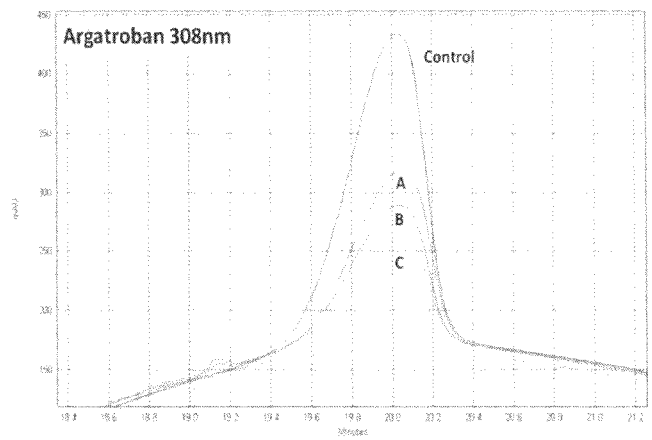
FIGS. 3A and 3B shows the photo-degradation profile of argatroban at 308 nm.
Figure 3B:
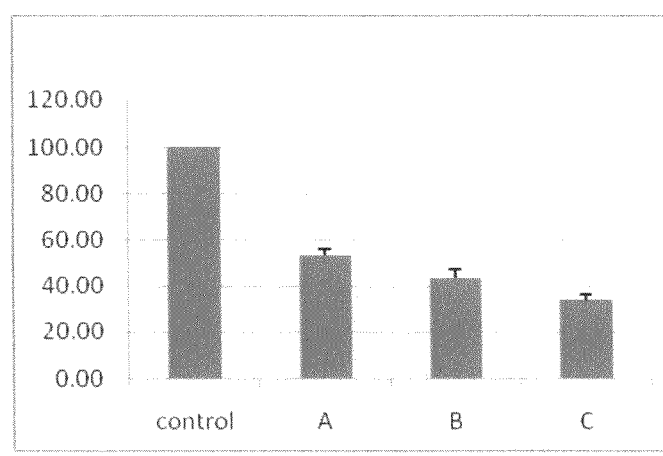

FIGS. 3A and 3B depict a similar set of observations for Argatroban exposure to $UV_{308}$. FIG. 3A shows HPLC traces of exposures A-C in relation to a control (unexposed 50 μg/mL Argatroban) and a saline blank. FIG. 3B is a graphical representation of the loss in peak height associated with the exposure of Argatroban to $UV_{308}$ expressed as % relative to control with standard deviations.

This data suggests that 'exposure A' at $UV_{308}$ has approximately the same impact as 'exposure C' at $UV_{282}$. FIG. 4 shows representative traces reflecting an identical pattern of photodegradation products at $UV_{282}$ and $UV_{308}$ in the two sets of experiments exemplified in FIGS. 2 and 3.

Tirofiban Exposure to $UV_{282\,nm}$

Figure 5A:
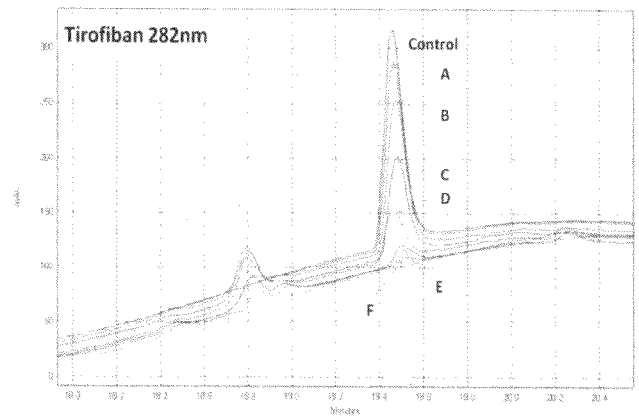
FIGS. 5A-5B show the photo-degradation profile of tirofiban at $UV_{282\ nm}$.
Figure 5B:
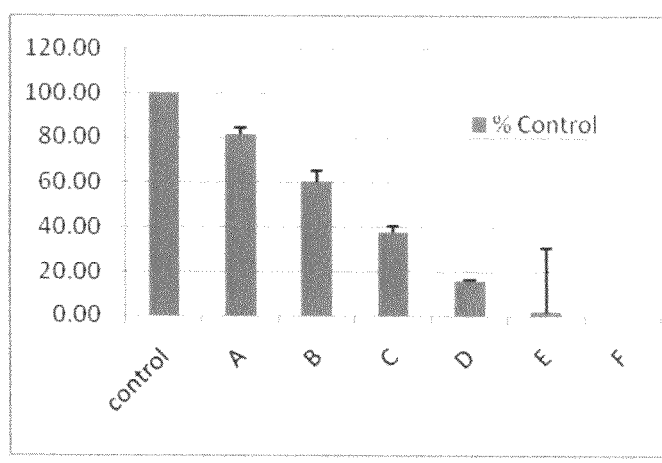

Tirofiban exposure to $UV_{282\,nm}$ provided a graduated photodegradation profile, as shown in FIGS. 5A and 5B. FIG. 5A shows HPLC traces of exposures A-F in reference to a control (unexposed 5 μg/mL Tirofiban) and a saline blank. FIG. 5B is a graphical representation of the loss in peak height associated with the exposure to $UV_{308}$ expressed as % relative to a control with standard deviations shown. Traces E and F were below the LLOQ for the assay.

Dose-dependent $UV_{282}$ photodegradation for Tirofiban was observed as follows: Control—100%; exposure A—81.2%; exposure B—59.9%; exposure C—37.7%; exposure D—15.4%; exposure E—1.5%; and exposure F—indeterminate. Four discernable degradation products were observed at 20.1', 18.7', 18.2°, and 17.5°, with the 18.2° peak (corresponding to exposure C) being the first appearing and most intense. An examination of the full spectrum ($A_{295-700\,nm}$) failed to reveal absorptive species at any other wavelengths.

Tirofiban Exposure to $UV_{308\ nm}$

Figure 6A:
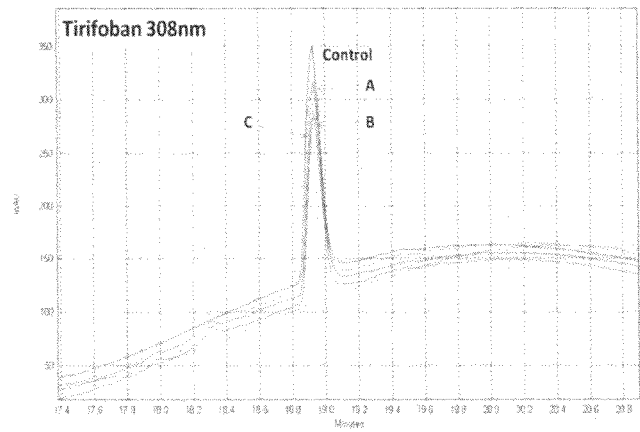
FIGS. 6A-6B show the photo-degradation profile of Tirofiban at $UV_{308}$.
Figure 6B:
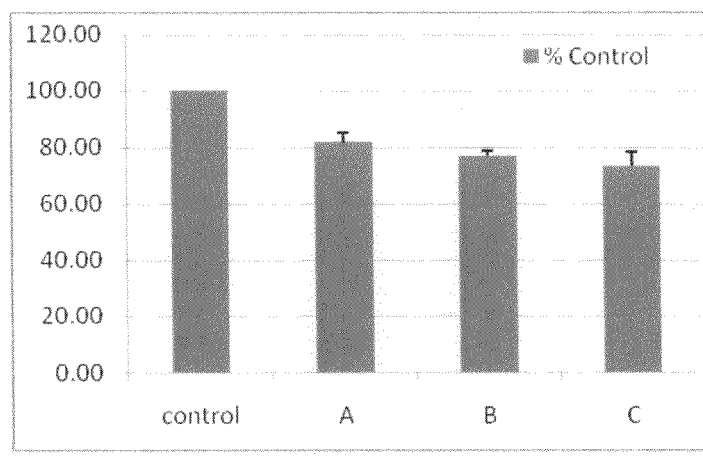

As shown in FIGS. 6A and 6B, the results for Tirofiban exposure to $UV_{308}$ followed a dissimilar trend as seen with Argatroban exposure at $UV_{308}$. That is, there was little photodegradation of the Tirofiban at $UV_{308}$. FIG. 6A shows HPLC traces of exposures A-C in reference to a control (unexposed 5 μg/mL Tirofiban) and a saline blank. FIG. 6B is a graphical representation of the loss in peak height associated with exposure to $UV_{308}$ expressed as % relative to control with standard deviations shown. The degradation profile was as follows: Exposure A—81.2%, B—76.9%, and C—73.0% relative to control.

Eptifibatide Exposure to $UV_{282\ nm}$

Figure 7A:
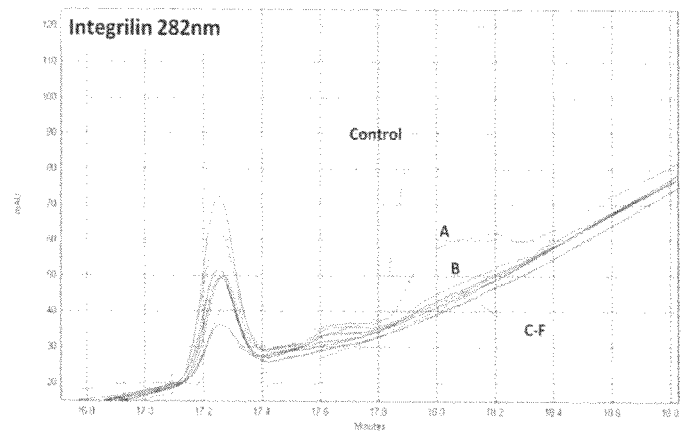
FIGS. 7A-7B show the photo-degradation profile of eptifibatide at $UV_{282\ nm}$.
Figure 7B:
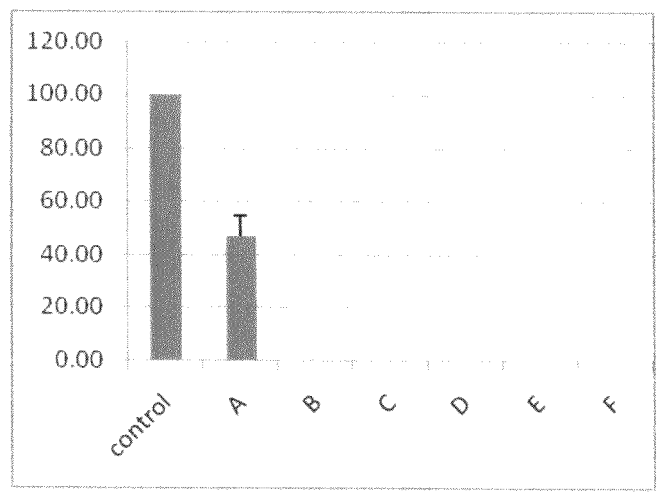

As shown in FIGS. 7A and 7B, Eptifibatide (INTEGRILIN®) exposure to $UV_{282\ nm}$ provided a faster photodegradation profile than the other compounds tested. FIG. 7A shows HPLC traces of exposures A-F in reference to a control (unexposed 5 μg/mL Eptifibatide) and a saline blank. FIG. 7B is a graphical representation of the loss in peak height associated with the exposure to $UV_{308}$ expressed as % relative to control. Exposure A was 47.0% relative to control, with the remainder of the exposures being below the LLOD. Notably, an additional species at 17.3 appeared to grow more intense with the initial exposures, but did not increase in intensity at higher exposures. It is possible this product degraded further, though there is no evidence of this in the remainder of the chromatogram. No other absorptive species was observed when examined on full spectrum scan ($A_{295-700\ nm}$). Exposure at $UV_{308}$ resulted in substantial photodegradation, but to a lesser extent than at $UV_{282}$ (assuming dosages are equivalent).

Eptifibatide Exposure to $UV_{308\ nm}$

Figure 8A:
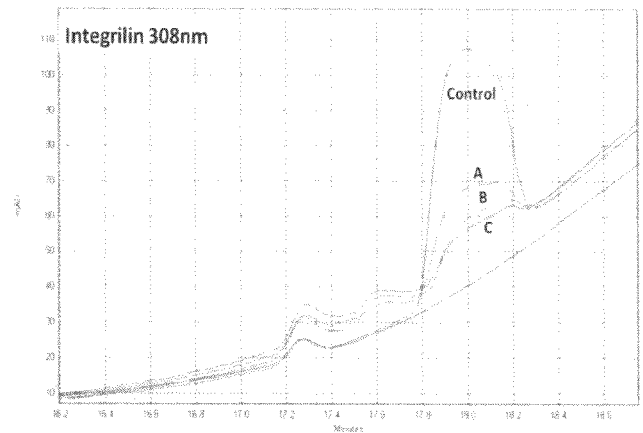
FIGS. 8A-8B show the photo-degradation profile of eptifibatide at $UV_{308\ nm}$.
Figure 8B:
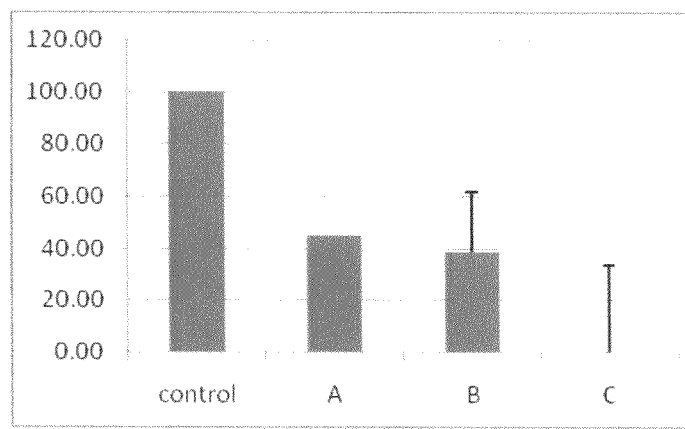

FIGS. 8A and 8B shows a photodegradation profile of Eptifibatide (INTEGRILIN®) at $UV_{308\ nm}$. FIG. 8A shows HPLC traces of exposures A-C in reference to a control (unexposed 5 μg/mL Eptifibatide) and a saline blank. FIG. 8B is a graphical representation of the loss in peak height associated with the exposure to $UV_{308}$ expressed as relative to control and with standard deviations shown. For Eptifibatide, similar degradation products were observed at either wavelength.

Photodegradation of the three agents proceeded in a similar nature independent of wavelength used, with degradation products noted in the results. Assuming the alpha-numeric codes for dosages were equivalent, the relative stabilities are as follows:

$UV_{282}$: Argatroban>Tirofiban>>Eptifibatide
$UV_{308}$: Tirofiban>>Argatroban>>Eptifibatide The above description is for the purpose of teaching the person of ordinary skill in the art how to practice the present invention, and it is not intended to detail all those obvious modifications and variations of it which will become apparent to the skilled worker upon reading the description. It is intended, however, that all such obvious modifications and variations be included within the scope of the present invention, which is defined by the following claims. The claims are intended to cover the claimed components and steps in any sequence which is effective to meet the objectives there intended, unless the context specifically indicates the contrary.

What is claimed is:

1. A preserved platelet composition, comprising:
   platelets;
   an effective amount of a photosensitizer for pathogen inactivation;
   a platelet activation inhibitor; and
   an anticoagulant,
   wherein the platelet activation inhibitor is selected from the group consisting of eptifibatide, tirofiban, abciximab, lefradafiban, sibrafiban, orbofiban, xemilofiban, lotrafiban, XJ757 and XR299, wherein the anticoagulant is a direct inhibitor of factor Xa or factor IIa,
   wherein the preserved platelet composition is sterilized by exposure to a radiation at a wavelength that sensitizes the photosensitizer, and wherein the platelet composition is substantially free of red blood cells.

2. The platelet preservation composition of claim 1, wherein the photosensitizer comprises riboflavin, psoralen or methylene blue.

3. The composition of claim 1, wherein the anticoagulant is selected from the group consisting of DX-9065a, RPR-120844, BX-807834, SEL-1915, SEL-2219, SEL-2489 and SEL-2711.

4. The composition of claim 1, wherein the anticoagulant is selected from the group consisting of DUP714, hirulog and melgatran.

5. The composition of claim 1, further comprising a hemoglobin-based oxygen carrier.

* * * * *